United States Patent
Fung et al.

(10) Patent No.: US 10,456,499 B2
(45) Date of Patent: Oct. 29, 2019

(54) ADHESIVE ARTICLES FOR MEDICAL APPLICATIONS

(71) Applicant: 3M INNOVATIVE PROPERTIES COMPANY, St. Paul, MN (US)

(72) Inventors: Simon S. Fung, Woodbury, MN (US); David T. Amos, St. Paul, MN (US); Junkang J. Liu, Woodbury, MN (US); Timothy M. Dietz, Mendota Heights, MN (US); Jing Ma, Shanghai (CN); Charles W. Opp, Cottage Grove, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 14/400,454

(22) PCT Filed: May 16, 2013

(86) PCT No.: PCT/US2013/041361
§ 371 (c)(1),
(2) Date: Nov. 11, 2014

(87) PCT Pub. No.: WO2013/173588
PCT Pub. Date: Nov. 21, 2013

(65) Prior Publication Data
US 2015/0165087 A1    Jun. 18, 2015

Related U.S. Application Data

(60) Provisional application No. 61/648,665, filed on May 18, 2012.

(51) Int. Cl.
| | |
|---|---|
| *A61L 24/04* | (2006.01) |
| *C09J 183/08* | (2006.01) |
| *A61M 25/02* | (2006.01) |
| *C08L 83/00* | (2006.01) |
| *C09J 7/38* | (2018.01) |
| *C09J 7/29* | (2018.01) |
| *C09J 7/21* | (2018.01) |
| *C08G 77/26* | (2006.01) |

(52) U.S. Cl.
CPC .......... *A61L 24/046* (2013.01); *A61M 25/02* (2013.01); *C08L 83/00* (2013.01); *C09J 7/21* (2018.01); *C09J 7/29* (2018.01); *C09J 7/38* (2018.01); *C09J 183/08* (2013.01); *A61M 2025/0266* (2013.01); *C08G 77/26* (2013.01); *C09J 2201/20* (2013.01); *C09J 2400/263* (2013.01); *C09J 2400/28* (2013.01); *C09J 2433/006* (2013.01); *C09J 2475/006* (2013.01); *C09J 2477/006* (2013.01); *C09J 2483/00* (2013.01); *C09J 2483/006* (2013.01)

(58) Field of Classification Search
CPC .......... A61L 15/58; A61L 15/26; C08L 71/02
See application file for complete search history.

(56) References Cited

U.S. PATENT DOCUMENTS

| | | |
|---|---|---|
| 3,437,622 A | 4/1969 | Dhal |
| 3,645,835 A | 2/1972 | Hodgson |
| 3,718,712 A | 2/1973 | Tushaus |
| 4,060,664 A | 11/1977 | McGuire |
| 4,366,814 A * | 1/1983 | Riedel ............... A61L 15/24 |
| | | 428/197 |
| 4,595,001 A | 6/1986 | Potter |
| 4,900,474 A | 2/1990 | Terae |
| 5,028,679 A | 7/1991 | Terae |
| 5,088,483 A | 2/1992 | Heinecke |
| 5,118,775 A | 6/1992 | Inomata |
| 5,160,315 A | 11/1992 | Heinecke |
| 5,209,971 A | 5/1993 | Babu |
| 5,214,119 A | 5/1993 | Leir |
| 5,236,997 A | 8/1993 | Fujiki |
| 5,461,134 A | 10/1995 | Leir |
| 5,512,650 A | 4/1996 | Leir |
| 5,514,730 A | 5/1996 | Mazurek |
| 5,591,820 A | 1/1997 | Kydonieus |
| 5,866,222 A | 2/1999 | Seth |
| 5,891,076 A | 4/1999 | Fabo |
| 6,407,195 B2 | 6/2002 | Sherman |
| 7,153,924 B2 | 12/2006 | Kuepfer |
| 2003/0211317 A1 | 11/2003 | Sheridan |

(Continued)

FOREIGN PATENT DOCUMENTS

| | | |
|---|---|---|
| GB | 1072891 | 6/1967 |
| JP | 2000-265134 | 9/2000 |

(Continued)

OTHER PUBLICATIONS

Final Rejection of U.S. Appl. No. 13/988,244, dated Jul. 28, 2016.*
Tyagi, "Segmented Organosiloxane Copolymers: 2. Thermal and Mechanical Properties of Siloxane-Urea Copolymers", Polymer, Dec. 1984, vol. 25, pp. 1807-1816.
International Search Report for PCT International Application No. PCT/US2013/041361 dated Aug. 21, 2013, 4 pages.

*Primary Examiner* — Victor S Chang

(74) *Attorney, Agent, or Firm* — Jeffrey M. Olofson

(57) ABSTRACT

Adhesive articles suitable for use in medical applications include a siloxane-based pressure sensitive adhesive layer, and a breathable conformable backing having a first surface and a second surface. The siloxane-based pressure sensitive adhesive layer is coated on the first surface of the breathable conformable backing, and the second surface of the breathable conformable backing comprises a treated surface. The siloxane-based pressure sensitive adhesive layer can be attached to skin and other adhesive articles can be releasably adhered to the treated surface to form adhesive constructions.

20 Claims, No Drawings

(56) References Cited

U.S. PATENT DOCUMENTS

| | | |
|---|---|---|
| 2007/0148475 A1 | 6/2007 | Sherman |
| 2010/0307513 A1 | 12/2010 | Svensby |
| 2010/0331785 A1 | 12/2010 | Fabo |
| 2011/0206924 A1 | 8/2011 | Liu |
| 2011/0212325 A1 | 9/2011 | Determan |
| 2013/0040126 A1* | 2/2013 | Pett .......................... C09D 1/00 428/312.6 |
| 2014/0287642 A1* | 9/2014 | Kumar ................ C08F 283/12 442/290 |

FOREIGN PATENT DOCUMENTS

| | | |
|---|---|---|
| JP | 2004-229830 | 8/2004 |
| WO | WO 1996-34028 | 10/1996 |
| WO | WO 1996-34030 | 10/1996 |
| WO | WO 1996-35458 | 11/1996 |
| WO | WO 1997-40103 | 10/1997 |
| WO | WO 1998-17726 | 4/1998 |
| WO | WO 2000-068336 | 11/2000 |
| WO | WO 2000-75210 | 12/2000 |
| WO | WO 2004-111151 | 12/2004 |
| WO | WO 2006-003853 | 1/2006 |
| WO | WO 2006-020708 | 2/2006 |
| WO | WO 2009-058466 | 5/2009 |
| WO | WO 2010-080679 | 7/2010 |
| WO | WO 2011-109672 | 9/2011 |
| WO | WO 2012-033456 | 3/2012 |
| WO | WO 2013-096530 | 6/2013 |

\* cited by examiner

ADHESIVE ARTICLES FOR MEDICAL APPLICATIONS

CROSS REFERENCE TO RELATED APPLICATIONS

This application is a national stage filing under 35 U.S.C. 371 of PCT/US2013/041361, filed May 16, 2013, which claims priority to U.S. Provisional Application No. 61/648, 665, filed May 18, 2012, the disclosure of which is incorporated by reference in its/their entirety herein.

FIELD OF THE DISCLOSURE

This disclosure relates to adhesive articles, such as tapes, that are useful in medical applications.

BACKGROUND

A wide range of adhesive articles are used in medical applications. These adhesive articles include gels used to attach electrodes and other sensing devices to the skin of a patient, a wide range of tapes to attach medical devices to a patient, and adhesive dressings used to cover and protect wounds.

Many of the adhesive articles use pressure sensitive adhesives. Pressure sensitive adhesives are well known to one of ordinary skill in the art to possess certain properties at room temperature including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as pressure sensitive adhesives are polymers designed and formulated to exhibit the requisite viscoelastic properties resulting in a desired balance of tack, peel adhesion, and shear strength. The most commonly used polymers for preparation of pressure sensitive adhesives are natural rubber, synthetic rubbers (e.g., styrene/butadiene copolymers (SBR) and styrene/isoprene/styrene (SIS) block copolymers), various (meth)acrylate (e.g., acrylate and methacrylate) copolymers, and silicones.

One problem with using adhesive articles for medical applications is that the removal of adhesive article can cause trauma to the skin. This is particularly troublesome in patients with sensitive skin, such as infants and the elderly, and can become severe with chronic patients where adhesive articles are repeatedly attached and removed over a long term period.

Various attempts have been made to mitigate this problem with adhesive articles. In particular, health care professionals utilize removal techniques to mitigate skin trauma. One way to mitigate trauma to the skin is to remove the adhesive article using a slow peel at a high angle to avoid stretching the skin. Another way to mitigate trauma, when the adhesive article is stretchable, is to pull straight out (as close to a 0° angle as possible) to induce stretch releasing of the adhesive layer from the skin. Also, manufactures of adhesive articles have developed articles that mitigate skin trauma. So called "gentle-to-skin adhesives" have been developed that provide sufficient adhesion to skin to adhere the adhesive article to the skin, but do not strip off skin cells significantly when removed.

A variety of gentle-to-skin articles and dressings that use gentle-to-skin adhesives have been described. A gentle-to-skin adhesive is described in US Patent Publication No. 2011/0212325 (Determan et al.) which describes an electron beam and gamma radiation crosslinked silicone gel adhesive that may use either nonfunctional or functional poly diorganosiloxanes. In the European Patent No. EP 2,001,424 (Cotton), adhesive laminate dressings are described that include a hydrophobic gel adhesive useful as the skin contact layer, and also contain a structural layer having the gel adhesive on one side and a pressure sensitive adhesive on the other side. Also, U.S. Pat. No. 5,891,076 (Fabo) describes a hypertrophic scar dressing that includes silicone-gel on that side of the dressing which lies against the user's skin and a flexible carrier sheet embodied within the silicone-gel such that the gel forms continuous layers on both sides of the carrier, and US Patent Publication No. 2010/0331785 (Fabo et al.) describes a dressing that includes a liquid impermeable film layer coated with a skin friendly adhesive on the side intended to adhere to the skin.

Additionally devices for affixing medical articles have been described. In US Patent Publication No. 2010/0307513 (Svensby et al.) a component for affixing an article of a medical-technical nature to skin is described that includes a layer of support material coated on one side (the side to be adhered to skin) with a layer of skin-friendly, soft pressure sensitive adhesive, and a fastening area on the top face of the support material layer. PCT Publication No. WO 2012/033456 describes a fixation device for retaining a skin penetrating medical device on the skin of a patient. The fixation device includes a retaining component that includes a support layer having an adhesive coating and a landing zone component adapted to be adhesively attached to the skin around the point of penetration.

SUMMARY

Disclosed herein are adhesive articles, adhesive constructions and methods of preparing adhesive constructions. In some embodiments, the adhesive articles comprise a siloxane-based pressure sensitive adhesive layer, and a breathable conformable backing having a first surface and a second surface. The siloxane-based pressure sensitive adhesive layer is coated on the first surface of the breathable conformable backing, and the second surface of the breathable conformable backing comprises a treated surface. The treated surface is not a pressure sensitive adhesive, but the treated surface provides increased adhesion to non-siloxane-based pressure sensitive adhesives when compared to the adhesion to the same backing without the treated surface.

Also disclosed are adhesive constructions. In some embodiments, the adhesive constructions comprise a first adhesive article and a second adhesive article. The first adhesive article comprises the adhesive articles described above. The second adhesive article is adhered to the treated surface of the first adhesive article. In some embodiments, the second adhesive article comprises a backing layer, and a nonsiloxane-based pressure sensitive adhesive layer. The adhesive construction may also further comprise a medical article located between the first adhesive article and the second adhesive article. Examples of medical articles include a cannula, tubing, a catheter, a dressing, a drape or a device for holding a medical device.

In other embodiments of adhesive constructions comprising a first adhesive article and a second adhesive article, the first adhesive article comprises an adhesive layer coated on the first surface of a breathable conformable backing, and the second surface of the breathable conformable backing comprises a treated surface. The treated surface is not a pressure sensitive adhesive, but the treated surface provides increased adhesion to non-siloxane-based pressure sensitive adhesives when compared to the adhesion to the same backing without the treated surface. The second adhesive article is adhered to the treated surface of the first adhesive article. The first adhesive article has an adhesion to skin that is less than the adhesion to skin of the second adhesive article.

The adhesive constructions may be prepared by the method of providing a first adhesive article, where the first adhesive article comprises the adhesive articles described above, applying the first adhesive article to a skin surface, providing a second adhesive article, and applying the second adhesive article to the treated surface of the first adhesive article.

DETAILED DESCRIPTION

The widespread use of adhesives, especially pressure sensitive adhesives, in medical applications has led to the development of pressure sensitive adhesives that are gentle to the skin. This can ease the trauma associated with removal, but tissue damage can still occur from repeated attachment and removal of adhesive articles. Therefore it is desirable to have an adhesive article such as a "platform tape". A platform tape is an adhesive article that can be attached to the skin and provide a working surface to which other adhesive articles could be attached and removed without the other adhesive articles having to contact the skin. The other adhesive articles that could be attached to the platform tape include a wide variety of medical tapes and other medical devices.

Adhesive tapes generally have a tape backing with a layer of pressure sensitive adhesive coated on at least a portion of at least one major surface of the backing. Many tapes are supplied as rolls, where the adhesive layer contacts the non-adhesive "back" side of the backing upon being rolled up. Often this non-adhesive surface of the backing has a low adhesion or release coating on it to permit the roll to be unwound. These low adhesion coatings are often called "low adhesion backsizes" or LABs. Many factors control whether an LAB coating is necessary or desirable, including the nature of the adhesive, the composition and topography of the backing, and the desired use for the tape article. For example, some polyolefinic backings have a sufficiently low surface energy that an LAB coating is not required when used with some classes of pressure sensitive adhesives.

For some tape uses, the presence of LABs can be detrimental. For example, masking tapes are often used to mask areas to be painted. Upon completion of the painting, the masking tape is removed. In some instances, when LAB coatings are used on the masking tape, the paint does not adhere well to the LAB coated surface and can run or flake off to contaminate the painted surface.

Similarly, a variety of tapes are designed to wrap upon themselves in use. Examples of these types of tapes are athletic tapes, duct tapes, electrical tapes, as well as a variety of medical tapes. With these tapes, the LAB coating must provide sufficiently easy release to permit facile unwinding of the tape, and yet must adhere sufficiently strongly to the adhesive to permit the tape to wrapped upon itself and retain the adhesion throughout the period of use of the tape.

For platform tapes, it may be desirable that the back side of the tape (i.e. the side on which the adhesive is not coated), provide a surface to which a variety of tapes and adhesive articles adhere well. However, if it is to be supplied as a roll, the adhesion of the siloxane-based pressure sensitive adhesive should not adhere too strongly to permit the roll to be unwound.

Adhesive articles of this disclosure are suitable for use as platform tapes. These adhesive articles comprise a breathable conformable backing with a first surface and a second surface, a siloxane-based pressure sensitive adhesive layer disposed on the first surface of the breathable conformable backing, and a treated surface on the second surface of the breathable conformable backing. The treated surface is not a pressure sensitive adhesive layer but it provides increased adhesion to non-siloxane-based pressure sensitive adhesives when compared to the adhesion to the same backing without the treated surface.

Also disclosed are methods of using these adhesive constructions as platform tapes, that is to say to adhere the platform tape to the skin and attach additional adhesive articles to the platform tape. The additional adhesive articles can be attached and removed without disrupting the adhesion of the platform tape to skin. This can be particularly advantageous with medical tapes that have a relatively high adhesion for skin and if applied to skin would cause skin trauma or irritation when removed. Because the tape is applied to the platform tape and not to skin, these high adhesion to skin tapes can be used without causing damage to the skin.

The term "adhesive" as used herein refers to polymeric compositions useful to adhere together two adherends. Examples of adhesives are pressure sensitive adhesives.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

The term "siloxane-based" as used herein refers to polymers that contain units with dialkyl or diaryl siloxane ($-SiR_2O-$) repeating units. The siloxane-based polymers may be segmented copolymers or polysiloxane polymers. The terms silicone and siloxane are used interchangeably.

The term "segmented copolymer" refers to a copolymer of linked segments, each segment constitutes primarily a single structural unit or type of repeating unit.

The term "urethane-based" as used herein refers to polymers that contain at least some urethane linkages ($-NH-(CO)-O-$ where (CO) represents a carbonyl group $C=O$). The polymers may contain only urethane linkages or may have additional types of linkages.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "heteroalkylene" refers to a divalent group that includes at least two alkylene groups connected by a thio, oxy, or —NR— where R is alkyl. The heteroalkylene can be linear, branched, cyclic, substituted with alkyl groups, or combinations thereof. Some heteroalkylenes are poloxyy-alkylenes where the heteroatom is oxygen such as for example, —$CH_2CH_2(OCH_2CH_2)_nOCH_2CH_2$—.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "aralkylene" refers to a divalent group of formula —$R^a$—$Ar^a$— where $R^a$ is an alkylene and $Ar^a$ is an arylene (i.e., an alkylene is bonded to an arylene).

The term "(meth)acrylate" refers to monomeric acrylic or methacrylic esters of alcohols. Acrylate and methacrylate monomers are referred to collectively herein as "(meth)acrylate" monomers. Materials that are described as "(meth)acrylate-based" contain at least some (meth)acrylate monomers and may contain additional co-monomers.

The terms "free radically polymerizable" and "ethylenically unsaturated" are used interchangeably and refer to a reactive group which contains a carbon-carbon double bond which is able to be polymerized via a free radical polymerization mechanism.

Disclosed herein are adhesive articles comprising a siloxane-based pressure sensitive adhesive layer; and a breathable conformable backing comprising a first surface and a second surface, wherein the siloxane-based pressure sensitive adhesive layer is coated on the first surface of the breathable conformable backing, and the second surface of the breathable conformable backing comprises a treated surface, wherein the treated surface is not a pressure sensitive adhesive and wherein the treated surface provides increased adhesion to non-siloxane-based pressure sensitive adhesives when compared to the adhesion to the same backing without the treated surface.

A wide variety of siloxane-based pressure sensitive adhesives are suitable for use with the adhesive articles of this disclosure. The siloxane-based pressure sensitive adhesive comprises an elastomeric siloxane polymer and may also comprise a tackifying resin. The elastomeric siloxane polymer can be prepared from an amine-functional polysiloxane, a hydroxyl-functional polysiloxane, a hydride-functional polysiloxane, an alkoxysilane-functional polysiloxane, a vinyl-functional polysiloxane, an allyl-functional polysiloxane, a (meth)acrylate-functional polysiloxane, a non-functional polysiloxane or a combination thereof. Generally, the elastomeric siloxane polymer is prepared from a linear material described by Formula 1 below, illustrating a siloxane backbone with aliphatic and/or aromatic substituents:

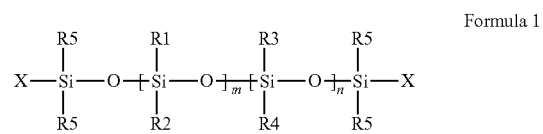

Formula 1 wherein R1, R2, R3, and R4 are independently selected from the group consisting of an alkyl group, an aryl group and a functional group, each R5 is an alkyl group, each X is a functional or non-functional group, and n and m are integers, and at least one of m or n is not zero. In some embodiments, one or more of the alkyl or aryl groups may contain a halogen substituent, e.g., fluorine. For example, in some embodiments, one or more of the alkyl groups may be —$CH_2CH_2C_4F_9$.

When Formula 1 is an amine-functional polysiloxane X is —$NH_2$; when Formula 1 is a hydroxyl-functional polysiloxane X is —OH; when Formula 1 is a hydride-functional polysiloxane X is —H; when Formula 1 is an alkoxysilane-functional polysiloxane X is —OR and one or more R5 groups may additionally be an —OR group, where R is an alkyl or aryl group; when Formula 1 is a vinyl-functional polysiloxane X is a vinyl group (—HC=$CH_2$); when Formula 1 is an allyl-functional polysiloxane X is an allyl group (—$CH_2$—CH=$CH_2$); when Formula 1 is a (meth)acrylate-functional polysiloxane X is a (meth)acrylate group of the general formula (—(CO)CR=$CH_2$, where (CO) is a carbonyl group C=O, and R is an H or a methyl group); when Formula 1 is a non-functional polysiloxane, X is an R5 group.

The polysiloxanes of Formula 1 can be used to prepare a wide range of elastomeric siloxane polymers. For example, amine-functional polysiloxanes can be used to prepare urea-based siloxane copolymers, oxamide-based siloxane copolymers, and amide-based siloxane copolymers. Hydroxyl-functional polysiloxanes can be used to prepare urethane-based siloxane copolymers. Alkoxy-functional polysiloxanes can be moisture cured to form elastomeric siloxane polymers. Hydride-functional polysiloxanes can be co-reacted with vinyl-functional polysiloxanes to form elastomeric siloxane polymers. Additionally, vinyl-functional polysiloxanes, allyl-functional polysiloxanes, and (meth)acrylate-functional polysiloxanes can be cured individually or together by free radical polymerization to form elastomeric siloxane polymers.

A wide range of elastomeric siloxane polymers suitable for use as pressure sensitive adhesives have been prepared from polysiloxanes of Formula 1. One example of a useful class of siloxane elastomeric polymers is urea-based siloxane polymers such as siloxane polyurea block copolymers. Siloxane polyurea block copolymers include the reaction product of a polydiorganosiloxane diamine (also referred to as a siloxane diamine), a diisocyanate, and optionally an organic polyamine. Suitable siloxane polyurea block copolymers are represented by the repeating unit of Formula 2:

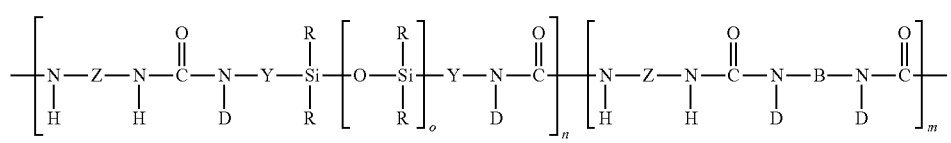

Formula 2 wherein each R is a moiety that, independently, is an alkyl moiety, having about 1 to 12 carbon atoms, and may be substituted with, for example, trifluoroalkyl or vinyl groups, a vinyl radical or a higher alkenyl radical, a cycloalkyl moiety having from about 6 to 12 carbon atoms and may be substituted with alkyl, fluoroalkyl, and vinyl groups, or an aryl moiety having from about 6 to 20 carbon atoms and may be substituted with, for example, alkyl, cycloalkyl, fluoroalkyl and vinyl groups or R is a perfluoroalkyl group as described in U.S. Pat. No. 5,028,679, or a fluorine-containing group, as described in U.S. Pat. No. 5,236,997, or a perfluoroether-containing group, as described in U.S. Pat. Nos. 4,900,474 and 5,118,775; typically, at least 50% of the R moieties are methyl radicals with the balance being monovalent alkyl or substituted alkyl radicals having from 1 to 12 carbon atoms, alkenyl radicals, phenyl radicals, or substituted phenyl radicals;

each Z is a polyvalent radical that is an arylene radical or an aralkylene radical having from about 6 to 20 carbon atoms, an alkylene or cycloalkylene radical having from about 6 to 20 carbon atoms, in some embodiments Z is 2,6-tolylene, 4,4'-methylenediphenylene, 3,3'-dimethoxy-4,4'-biphenylene, tetramethyl-m-xylylene, 4,4'-methylenedicyclohexylene, 3,5,5-trimethyl-3-methylenecyclohexylene, 1,6-hexamethylene, 1,4-cyclohexylene, 2,2,4-trimethylhexylene and mixtures thereof;

each Y is a polyvalent radical that independently is an alkylene radical of 1 to 10 carbon atoms, an aralkylene radical or an arylene radical having 6 to 20 carbon atoms;

each D is selected from the group consisting of hydrogen, an alkyl radical of 1 to 10 carbon atoms, phenyl, and a radical that completes a ring structure including B or Y to form a heterocycle;

where B is a polyvalent radical selected from the group consisting of alkylene, aralkylene, cycloalkylene, phenylene, heteroalkylene, including for example, polyethylene oxide, polypropylene oxide, polytetramethylene oxide, and copolymers and mixtures thereof;

m is a number that is 0 to about 1000;

n is a number that is at least 1; and p is a number that is at least 10, in some embodiments 15 to about 2000, or even 30 to 1500.

Useful siloxane polyurea block copolymers are disclosed in, e.g., U.S. Pat. Nos. 5,512,650, 5,214,119, 5,461,134, and 7,153,924 and PCT Publication Nos. WO 96/35458, WO 98/17726, WO 96/34028, WO 96/34030 and WO 97/40103.

Another useful class of elastomeric siloxane polymers that can be prepared from amine-functional polysiloxanes are oxamide-based polymers such as polydiorganosiloxane polyoxamide block copolymers. Examples of polydiorganosiloxane polyoxamide block copolymers are presented, for example, in US Patent Publication No. 2007/0148475. The polydiorganosiloxane polyoxamide block copolymer contains at least two repeat units of Formula 3.

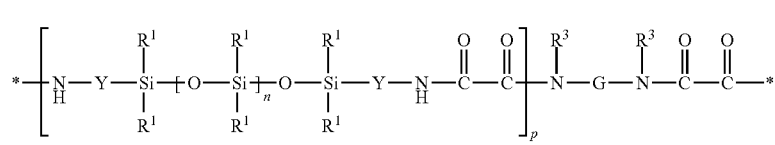

Formula 3

In this formula, each $R^1$ is independently an alkyl, haloalkyl, aralkyl, alkenyl, aryl, or aryl substituted with an alkyl, alkoxy, or halo, wherein at least 50 percent of the $R^1$ groups are methyl. Each Y is independently an alkylene, aralkylene, or a combination thereof. Subscript n is independently an integer of 40 to 1500 and the subscript p is an integer of 1 to 10. Group G is a divalent group that is the residue unit that is equal to a diamine of formula $R^3$HN-G-NHR$^3$ minus the two —NHR$^3$ groups. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3$HN-G-NHR$^3$ is piperazine or the like). Each asterisk (*) indicates a site of attachment of the repeat unit to another group in the copolymer such as, for example, another repeat unit of Formula 3.

Suitable alkyl groups for R' in Formula 3 typically have 1 to 10, 1 to 6, or 1 to 4 carbon atoms. Exemplary alkyl groups include, but are not limited to, methyl, ethyl, isopropyl, n-propyl, n-butyl, and iso-butyl. Suitable haloalkyl groups for $R^1$ often have only a portion of the hydrogen atoms of the corresponding alkyl group replaced with a halogen. Exemplary haloalkyl groups include chloroalkyl and fluoroalkyl groups with 1 to 3 halo atoms and 3 to 10 carbon atoms. Suitable alkenyl groups for $R^1$ often have 2 to 10 carbon atoms. Exemplary alkenyl groups often have 2 to 8, 2 to 6, or 2 to 4 carbon atoms such as ethenyl, n-propenyl, and n-butenyl. Suitable aryl groups for $R^1$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable aralkyl groups for $R^1$ usually have an alkylene group having 1 to 10 carbon atoms and an aryl group having 6 to 12 carbon atoms. In some exemplary aralkyl groups, the aryl group is phenyl and the alkylene group has 1 to 10 carbon atoms, 1 to 6 carbon atoms, or 1 to 4 carbon atoms (i.e., the structure of the aralkyl is alkylene-phenyl where an alkylene is bonded to a phenyl group).

At least 50 percent of the R' groups are methyl. For example, at least 60 percent, at least 70 percent, at least 80 percent, at least 90 percent, at least 95 percent, at least 98 percent, or at least 99 percent of the R' groups can be methyl. The remaining R' groups can be selected from an alkyl having at least two carbon atoms, haloalkyl, aralkyl, alkenyl, aryl, or aryl substituted with an alkyl, alkoxy, or halo.

Each Y in Formula 3 is independently an alkylene, aralkylene, or a combination thereof. Suitable alkylene groups typically have up to 10 carbon atoms, up to 8 carbon atoms, up to 6 carbon atoms, or up to 4 carbon atoms. Exemplary alkylene groups include methylene, ethylene, propylene, butylene, and the like. Suitable aralkylene groups usually have an arylene group having 6 to 12 carbon atoms bonded to an alkylene group having 1 to 10 carbon atoms. In some exemplary aralkylene groups, the arylene portion is phenylene. That is, the divalent aralkylene group is phenylene-alkylene where the phenylene is bonded to an alkylene having 1 to 10, 1 to 8, 1 to 6, or 1 to 4 carbon atoms. As used herein with reference to group Y, "a combination thereof" refers to a combination of two or more groups selected from an alkylene and aralkylene group. A combination can be, for example, a single aralkylene bonded to a single alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Each subscript n in Formula 3 is independently an integer of 40 to 1500. For example, subscript n can be an integer up to 1000, up to 500, up to 400, up to 300, up to 200, up to 100, up to 80, or up to 60. The value of n is often at least 40, at least 45, at least 50, or at least 55. For example, subscript n can be in the range of 40 to 1000, 40 to 500, 50 to 500, 50 to 400, 50 to 300, 50 to 200, 50 to 100, 50 to 80, or 50 to 60.

The subscript p is an integer of 1 to 10. For example, the value of p is often an integer up to 9, up to 8, up to 7, up to 6, up to 5, up to 4, up to 3, or up to 2. The value of p can be in the range of 1 to 8, 1 to 6, or 1 to 4.

Group G in Formula 3 is a residual unit that is equal to a diamine compound of formula $R^3HN-G-NHR^3$ minus the two amino groups (i.e., —$NHR^3$ groups). Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN-G-NHR^3$ is piperazine). The diamine can have primary or secondary amino groups. In most embodiments, $R^3$ is hydrogen or an alkyl. In many embodiments, both of the amino groups of the diamine are primary amino groups (i.e., both $R^3$ groups are hydrogen) and the diamine is of formula $H_2N-G-NH_2$.

In some embodiments, G is an alkylene, heteroalkylene, polydiorganosiloxane, arylene, aralkylene, or a combination thereof. Suitable alkylenes often have 2 to 10, 2 to 6, or 2 to 4 carbon atoms. Exemplary alkylene groups include ethylene, propylene, butylene, and the like. Suitable heteroalkylenes are often polyoxyalkylenes such as polyoxyethylene having at least 2 ethylene units, polyoxypropylene having at least 2 propylene units, or copolymers thereof. Suitable polydiorganosiloxanes include the polydiorganosiloxane diamines of Formula 1, which are described above, minus the two amino groups. Exemplary polydiorganosiloxanes include, but are not limited to, polydimethylsiloxanes with alkylene Y groups. Suitable aralkylene groups usually contain an arylene group having 6 to 12 carbon atoms bonded to an alkylene group having 1 to 10 carbon atoms. Some exemplary aralkylene groups are phenylene-alkylene where the phenylene is bonded to an alkylene having 1 to 10 carbon atoms, 1 to 8 carbon atoms, 1 to 6 carbon atoms, or 1 to 4 carbon atoms. As used herein with reference to group G, "a combination thereof" refers to a combination of two or more groups selected from an alkylene, heteroalkylene, polydiorganosiloxane, arylene, and aralkylene. A combination can be, for example, an aralkylene bonded to an alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

The polydiorganosiloxane polyoxamide tends to be free of groups having a formula —$R^a$—(CO)—NH— where $R^a$ is an alkylene. All of the carbonylamino groups along the backbone of the copolymeric material are part of an oxalylamino group (i.e., the —(CO)—(CO)—NH— group). That is, any carbonyl group along the backbone of the copolymeric material is bonded to another carbonyl group and is part of an oxalyl group. More specifically, the polydiorganosiloxane polyoxamide has a plurality of aminoxalylamino groups.

Another useful class of elastomeric siloxane polymers is amide-based polysiloxane polymers. Such polymers are similar to the urea-based polymers, containing amide linkages (—N(D)-C(O)—) instead of urea linkages (—N(D)-C(O)—N(D)-), where C(O) represents a carbonyl group and D is a hydrogen or alkyl group.

Such polymers may be prepared from the polydiorganosiloxane diamine described above in Formula 1, the amide-based polymer can be prepared by reaction with a polycarboxylic acid or a poly-carboxylic acid derivative such as, for example di-esters. In some embodiments, an amide-based siloxane elastomer is prepared by the reaction of a polydiorganosiloxane diamine and dimethyl salicylate of adipic acid.

Another example of a useful class of elastomeric siloxane polymers is urethane-based siloxane polymers such as siloxane polyurea-urethane block copolymers. Siloxane polyurea-urethane block copolymers include the reaction product of a polydiorganosiloxane diamine (also referred to as siloxane diamine), a diisocyanate, and an organic polyol. Such materials are structurally very similar to the structure of Formula I except that the —N(D)-B—N(D)- links are replaced by —O—B—O— links. Examples are such polymers are presented, for example, in U.S. Pat. No. 5,214,119.

These urethane-based siloxane polymers are prepared in the same fashion as the urea-based siloxane polymers except that an organic polyol is substituted for an organic polyamine. Typically, since the reaction between an alcohol group and an isocyanate group is slower than the reaction between a amine group and an isocyanate group, a catalyst such as a tin catalyst commonly used in polyurethane chemistry, is used.

Another useful class of elastomeric siloxane polymers can be prepared by moisture curing of alkoxy-functional polysiloxanes. As mentioned above, only the X group of Formula 1 may be an alkoxy group, or one or both of the R5 groups may also be alkoxy groups. Examples of suitable —SiR5R5X units include trimethoxy silyl, dimethyl methoxy silyl, triethoxy silyl, methyl diethoxy silyl, and the like. These silyl alkoxy groups are subject to hydrolysis (that is to say they readily react with water) to form silanol groups such as for example —SiR5R5(OH). These silanol units can then further condense with other silanol units to siloxane linkages (—Si—O—Si—) and generate water.

Typically the moisture curing reaction is facilitated by a catalyst. Examples of suitable curing catalysts for this moisture curing reaction include alkyl tin derivatives (e.g., dibutyltindilaurate, dibutyltindiacetate, and dibutyltindioctoate commercially available as "T-series Catalysts" from Air Products and Chemicals, Inc. of Allentown, Pa.), and alkyl titanates (e.g., tetraisobutylorthotitanate, titanium acetylacetonate, and acetoacetic ester titanate commercially available from DuPont under the designation "TYZOR"). Other catalysts useful for the moisture curing reaction include acids, anhydrides, and lower alkyl ammonium salts thereof which include but are not limited to those selected from the group consisting of trichloroacetic acid, cyanoacetic acid, malonic acid, nitroacetic acid, dichloroacetic acid, difluoroacetic acid, trichloroacetic anhydride, dichloroacetic anhydride, difluoroacetic anhydride, triethylammonium trichloroacetate, trimethylammonium trichloroacetate, and mixtures thereof.

Examples of elastomeric siloxane polymers are described in U.S. Pat. No. 6,407,195 (Sherman et al.).

Yet another curing mechanism that can be used to prepare elastomeric siloxane polymers is the addition reaction (typically catalyzed by a metal catalyst such a platinum) between a vinyl group (—CH=$CH_2$) and a silyl hydride (—Si—H) group. In this reaction, the Si—H adds across the double bond to form new C—H and Si—C bonds. This process is described, for example, in PCT Publication No. WO 2000/068336 (Ko et al.), and PCT Publication Nos. WO 2004/111151 and WO 2006/003853 (Nakamura).

Additionally, elastomeric siloxane polymers can be prepared by the free radical polymerization of ethylenically unsaturated siloxanes such as (meth)acrylate functional siloxanes and/or vinyl-functional or allyl-functional siloxanes. (Meth)acrylate-functional siloxanes can be prepared by, for example, the reaction of amine-functional siloxanes with isocyanate-functional (meth)acrylates. Typically, the (meth)acrylate-functional siloxane is co-polymerized with additional free radically polymerized monomers to form elastomeric siloxane polymers suitable for use as pressure sensitive adhesives. The free radical polymerization can be carried out under a variety of conditions using a variety of different types of free radical initiators. Photoinitiators have been found to be particularly suitable as describe in U.S. Pat. No. 5,514,730 (Mazurek).

Recently, gentle to skin adhesives have been described in US Patent Publication No. 2011/0212325 (Determan et al.) that can be prepared from non-functionalized polysiloxane materials. These materials are ones described by Formula 1 with X=R5, and ones described by Formula 1 where X=OH. The materials where X=OH are considered to be "Non-functionalized materials" because the hydroxyl groups are not used as "functional groups", that is to say that the polymerization reaction does not involve reaction with the hydroxyl groups. These "non-functional materials" have been found to polymerize upon exposure to electron beam or gamma radiation generate siloxane networks. In addition to the non-functionalized polysiloxane materials (where X=R5 or OH), the functionalized polysiloxane materials described above can also be polymerized in this way to generate siloxane networks. In other words, this polymerization method is very general and has the advantage of not requiring catalysts or initiators.

In some embodiments of the gentle to skin adhesives, each X and R5 comprises a methyl group, i.e., the nonfunctionalized poly diorganosiloxane material is terminated by trimethylsiloxy groups. In other embodiments, each R5 is a methyl and each X is a hydroxyl, such that the nonfunctionalized poly diorganosiloxane material is terminated by dimethylsilanol groups. In some embodiments, R1 and R2 are alkyl groups and n is zero, i.e., the material is a poly(dialkylsiloxane). In some embodiments, the alkyl group is a methyl group, i.e., poly(dimethylsiloxane) ("PDMS"). In some embodiments, R1 is an alkyl group, R2 is an aryl group, and n is zero, i.e., the material is a poly(alkylarylsiloxane). In some embodiments, R1 is methyl group and R2 is a phenyl group, i.e., the material is poly (methylphenylsiloxane). In some embodiments, R1 and R2 are alkyl groups and R3 and R4 are aryl groups, i.e., the material is a poly(dialkyldiarylsiloxane). In some embodiments, R1 and R2 are methyl groups, and R3 and R4 are phenyl groups, i.e., the material is poly(dimethyldiphenylsiloxane).

In some embodiments, the nonfunctionalized poly diorganosiloxane materials may be branched. For example, one or more of the R1, R2, R3, and/or R4 groups may be a linear or branched siloxane with alkyl or aryl (including halogenated alkyl or aryl) substituents and terminal R5 groups.

As used herein, "nonfunctional groups" are either alkyl or aryl groups consisting of carbon, hydrogen, and in some embodiments, halogen (e.g., fluorine) atoms, or hydroxyl groups that are not involved with the polymerization reaction. As used herein, a "nonfunctionalized poly diorganosiloxane material" is one in which the R1, R2, R3, R4, R5, and X groups are nonfunctional groups.

The nonfunctionalized poly diorganosiloxane materials are cured to elastomeric siloxane networks by exposure to an electron beam (E-beam), gamma radiation, or a combination thereof. This process is described in greater detail below.

However the elastomeric siloxane polymers are prepared, they may be blended with a tackifying resin to generate a pressure sensitive adhesive. In some embodiments, silicate tackifying resins may be used.

Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000-gm/mole, e.g., 500 to 15,000 gm/mole and generally R' groups are methyl groups.

MQ silicate tackifying resins are copolymeric resins where each M unit is bonded to a Q unit, and each Q unit is bonded to at least one other Q unit. Some of the Q units are bonded to only other Q units. However, some Q units are bonded to hydroxyl radicals resulting in $HOSiO_{3/2}$ units (i.e., "$T^{OH}$" units), thereby accounting for some siliconbonded hydroxyl content of the silicate tackifying resin.

The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD siloxane tackifying resins are terpolymers having M, Q and D units. In some embodiments, some of the methyl R' groups of the D units can be replaced with vinyl (CH2=CH—) groups ("$D^{Vi}$" units). MQT silicate tackifying resins are terpolymers having M, Q and T units.

Suitable silicate tackifying resins are commercially available from sources such as Dow Corning (e.g., DC 2-7066), Momentive Performance Materials (e.g., SR545 and SR1000), and Wacker Chemie AG (e.g., BELSIL TMS-803).

The siloxane-based pressure sensitive adhesives may be prepared by a variety of methods. In some embodiments, the elastomeric siloxane polymer is prepared and blended with a tackifying resin, such as those described above. In other embodiments, the reactants used to prepare the elastomeric siloxane polymer are mixed with the tackifying resin and the resulting mixture is then subjected to polymerization conditions to generate the elastomeric siloxane polymer in the presence of the tackifying resin.

In embodiments where the elastomeric siloxane polymer is prepared and then blended with a tackifying resin, the elastomeric siloxane polymers can be prepared by solvent-based processes, solventless processes or a combination thereof. Useful solvent-based processes are described in, e.g., Tyagi et al., "Segmented Organosiloxane Copolymers: 2. Thermal and Mechanical Properties of Siloxane-Urea Copolymers," Polymer, vol. 25, December, 1984, and U.S. Pat. No. 5,214,119. Useful methods of manufacturing elastomeric siloxane polymers are also described in, e.g., U.S. Pat. Nos. 5,512,650, 5,214,119, and 5,461,134, US Patent Publication No. 2007/0148475, and PCT Publication Nos. WO 96/35458, WO 98/17726, WO 96/34028, and WO 97/40103.

In some particularly suitable embodiments, the elastomeric siloxane polymer is generated from nonfunctionalized polysiloxane materials as described above. While these materials are described as nonfunctionalized polysiloxane materials, functionalized polysiloxane materials can be used in conjunction with the nonfunctionalized polysiloxane materials to generate the elastomeric siloxane polymers. In other words, while most of the reactive species that form the elastomeric siloxane polymer are materials of Formula 1 in which the X groups are R5 groups, some of the X groups may comprise functional groups. Additionally, any of R-groups on the siloxane backbone, that is to say, R1, R2, R3 or R4 can independently contain functional groups such as, for example, vinyl or hydride groups. In addition to functional R-groups, the R-groups may be nonfunctional groups, e.g., alkyl or aryl groups, including halogenated (e.g., fluorinated) alky and aryl groups. In some embodiments, the functionalized poly diorganosiloxane materials may be branched. For example, one or more of the R-groups may be a linear or branched siloxane with functional and/or non-functional substituents.

For ease of use and availability and cost reasons, typically non-functionalized poly diorganosiloxane materials are used to prepare the siloxane-based pressure sensitive adhesives of this disclosure. In some embodiments, the siloxane-based pressure sensitive adhesive is prepared by combining one or more poly diorganosiloxane materials (e.g., silicone oils or fluids), optionally with an appropriate tackifying resin, coating the resulting combination, and curing using electron beam (E-beam) or gamma irradiation. Generally, any known additives useful in the formulation of adhesives may also be included. The polysiloxane material, the tackifying resin, if present, and any optional additives may be combined by any of a wide variety of known means prior to being coated and cured. For example, in some embodiments, the various components may be pre-blended using common equipment such as mixers, blenders, mills, extruders, and the like.

In some embodiments, the materials may be dissolved in a solvent, coated, and dried prior to curing. In some embodiments, solventless compounding and coating processes may be used. In some embodiments, solventless coating may occur at about room temperature. For example, in some embodiments, the materials may have kinematic viscosity of no greater than 100,000 centistokes (cSt), e.g., no greater than 50,000 cSt. However, in some embodiments, hot melt coating processes such as extrusion may be used, e.g., to reduce the viscosity of higher molecular weight materials to values more suitable for coating. The various components may be added together, in various combinations or individually, through one or more separate ports of an extruder, blended (e.g., melt mixed) within the extruder, and extruded to form the hot melt coated composition. The coating may be made on, for example, a release liner or a carrier film.

Regardless of how it is formed, the coated compositions are radiation cured. In some embodiments, coating may be cured through exposure to E-beam irradiation. In some embodiments, the coating may be cured through exposure to gamma irradiation. In some embodiments, a combination of electron beam curing and gamma ray curing may be used. For example, in some embodiments, the coating may be partially cured by exposure to electron beam irradiation. Subsequently, the coating may be further cured by gamma irradiation.

A variety of procedures for E-beam and gamma ray curing are well-known. The cure depends on the specific equipment used, and those skilled in the art can define a dose calibration model for the specific equipment, geometry, and line speed, as well as other well understood process parameters.

Commercially available electron beam generating equipment is readily available. For the examples described herein, the radiation processing was performed on a Model CB-300 electron beam generating apparatus (available from Energy Sciences, Inc. (Wilmington, Mass.). Generally, a support film (e.g., polyester terephthalate support film) runs through a chamber. In some embodiments, a sample of uncured material with a liner (e.g., a fluorosilicone release liner) on both sides ("closed face") may be attached to the support film and conveyed at a fixed speed of about 6.1 meters/min (20 feet/min) In some embodiments, a sample of the uncured material may be applied to one liner, with no liner on the opposite surface ("open face"). Generally, the chamber is inerted (e.g., the oxygen-containing room air is replaced with an inert gas, e.g., nitrogen) while the samples are e-beam cured, particularly when open-face curing.

The uncured material may be exposed to E-beam irradiation from one side through a release liner or carrier film. For making a single layer laminating adhesive type tape, a single pass through the electron beam may be sufficient. Thicker samples, may exhibit a cure gradient through the cross section of the adhesive so that it may be desirable to expose the uncured material to electron beam radiation from both sides.

Commercially available gamma irradiation equipment includes equipment often used for gamma irradiation sterilization of products for medical applications. In some embodiments, such equipment may be used to cure, or partially cure the gentle to skin adhesives of the present disclosure.

Adhesive articles of this disclosure also comprise a breathable conformable backing, on which the adhesive layers described above are disposed. A wide range of breathable conformable backings are suitable for use in articles of this disclosure. Typically the breathable conformable backing comprises a woven or knit textile, a nonwoven, or a plastic.

In some embodiments, the breathable conformable backing comprises a high moisture vapor permeable film backings. Examples of such backings, methods of making such films, and methods for testing their permeability are described, for example, in U.S. Pat. Nos. 3,645,835 and 4,595,001. Typically such backings are porous materials.

Generally the backing is conformable to anatomical surfaces. As such, when the backing is applied to an anatomical surface, it conforms to the surface even when the surface is moved. Generally, the backing is also conformable to animal anatomical joints. When the joint is flexed and then returned to its unflexed position, the backing stretches to accommodate the flexion of the joint, but is resilient enough to continue to conform to the joint when the joint is returned to its unflexed condition.

Examples of particularly suitable backings can be found in U.S. Pat. Nos. 5,088,483 and 5,160,315, and include elastomeric polyurethane, polyester, or polyether block amide films. These films have a combination of desirable properties including resiliency, high moisture vapor permeability, and transparency.

The breathable conformable backing has the siloxane-based pressure sensitive adhesive coated on one major surface, and the other major surface is surface treated to modify the properties of the backing surface. This surface treatment provides increased adhesion to non-siloxane-based pressure sensitive adhesives when compared to the adhesion to the same backing without the treated surface.

In some embodiments, the treatment comprises a physical treatment. Examples of suitable physical treatments include flame treatment, corona treatment, plasma treatment and the like. In these treatments, the surface may be physically and chemically altered, but typically no new materials are deposited on the surface. The physical alteration of the surface may involve increasing the surface area as the result of surface topography changes. The chemical alteration of the surface may involve increasing the surface energy of the surface. A variety of different parameters can be used to control the physical alteration of the surface and give the desired surface characteristics. For example, with corona treatment, the vapor environment can be oxygen or nitrogen; with flame treatment the ratio of gas to oxygen can be varied; and with plasma treatment, a variety of different gases can be used.

In other embodiments, the treatment involves the application of a surface coating applied to at least a portion of the surface. Typically the coatings cover the entire backing surface, and generally are thin relative to the thickness of the backing. In some embodiments, the coating may not cover the entire backing surface and may be applied in the form of stripes, patterns or other discontinuous arrays. In still other embodiments, the treatment may involve a combination of physical treatment and application of a coating.

Typically the treatment involves the application of a coating. A wide variety of different coatings are suitable. While the coating increases the adhesion of a wide range of pressure sensitive adhesives, the coating itself is not a pressure sensitive adhesive. Generally, the coating comprises materials that are commonly referred to as "primers" or "adhesion promoters". Primers and adhesion promoters are materials that are applied as thin coatings on a surface and strongly adhere to the surface and provide a modified surface chemistry to the surface. Examples of suitable coating materials include polyamides, poly(meth)acrylates, chlorinated polyolefins, rubbers, chlorinated rubbers, polyurethanes, siloxanes, silanes, polyester, epoxies, polycarbodiimides, phenolics, and combinations thereof.

The coating material may be applied to the breathable conformable backing as a solventborne mixture, a waterborne mixture, or as a 100% solids composition. Typically the coating is applied as a solventborne or a waterborne mixture.

Examples of suitable commercially available coating materials include: the polyamide UNI-REZ available from Arizona Chemical; the polyacrylate RHOPLEX from Dow Chemical; the chlorinated polyolefins such as EASTMAN CP-343 available from Eastman Chemical, or SUPER-CHLON from Nippon Paper Chemicals; the synthetic rubber KRATON materials available from Kraton Polymers; the polyurethane NEO-REZ available from DSM; the siloxanes described in U.S. Pat. No. 5,866,222 (Seth et al.) and U.S. Patent Application Ser. No. 61/579,115 filed on Dec. 22, 2011, titled "Adhesive Article Including Primer Layer and Method of Making the Same"; the SILQUEST silane materials available from Momentive; the polyester EASTMAN AQ resins available from Eastman Chemical; the epoxy DER materials available from Dow Chemical; the polycarbodiimides described in U.S. Pat. No. 4,060,664; and the phenolic BKS resins from Georgia-Pacific.

In some embodiments, the coating composition comprises a film-forming resin and may additionally contain a wide variety of additional additives. The selection of the film forming resin or resins is affected by an array of properties including solubility of the resin, and the molecular weight and Tg of the polymer of polymers in the resin.

Various film-forming resins are known. Representative film-forming resins include acrylic resin(s), polyvinyl resin(s), polyester(s), polyacrylate(s), polyurethane(s) and mixtures thereof. Polyester resins include copolyester resins commercially available from Bostik Inc., Middleton, Mass. under the trade designation "VITEL 2300BG"; copolyester resins available from Eastman Chemical, Kingsport, Tenn. under the trade designation "EASTAR" as well as other polyester resins available from Bayer, Pittsburg, Pa. under the trade designations "MULTRON" and "DESMOPHEN"; Spectrum Alkyd & Resins Ltd., Mumbia, Maharshtra, India under the trade designation "SPECTRAALKYD" and Akzo Nobel, Chicago, Ill. under the trade designation "SETALIN" alkyd.

Solvent-based primer compositions comprise the base polymer admixed with a solvent. The solvent may be a single solvent or a blend of solvents. The solvent-based primer composition generally contains about 5 to about 60 parts by weight of the base polymer, more typically about 10 to about 40 parts base polymer or even about 10 to about 30 parts base polymer, with the remainder of the primer composition being solvent and optional additives.

Among the particularly suitable film forming resins are acrylic resins, polyvinyl resins and mixtures thereof. Various acrylic resins are know. In general, acrylic resins are prepared from various (meth)acrylate monomers such as polymethylmethacrylate (PMMA), methyl methacrylate (MMA), ethyl acrylate (EA), butyl acrylate (BA), butyl methacrylate (BMA), n-butyl methacrylate (n-BMA) isobutylmethacrylate (IBMA), polyethylmethacrylate (PEMA), etc. alone or in combination with each other. Exemplary acrylic resins include those commercially available from Rohm and Haas, Co., Philadelphia, Pa. under the trade designation "PARALOID" and from Ineos Acrylics, Cordova, Tenn. under the trade designation "ELVACITE" resins. Other suitable polyacrylic materials include those from S. C. Johnson, Racine, Wis. under the trade designation "JONCRYL" acrylics. Polyvinyl resins include vinyl chloride/vinyl acetate copolymers, such as available from Rohm and Haas, Co., Philadelphia, Pa. under the trade designation "ACRYLOID" and from available from Union Carbide Corp., a subsidiary of The Dow Chemical Company ("Dow"), Midland Mich. under the trade designation "VYHH" as well as vinyl chloride/vinyl acetate/vinyl alcohol terpolymers also commercially available from Union Carbide Corp. under the trade designation "UCAR VAGH". Other polyvinyl chloride resins are available from Occidental Chemical, Los Angeles, Calif.; BF Goodrich Performance Materials, Cleveland, Ohio; and BASF, Mount Olive, N.J.

Suitable water-based primers are generally emulsions or dispersions that are substantially free of water soluble base polymers as a major component. Water-based emulsions and dispersions are advantageous to reduce solvent emissions by employing primer compositions that are substantially free of volatile organic solvents. An exemplary water-based primer includes a crosslinked poly(meth)acrylate polymer such as a butyl acrylate/methyl methacrylate copolymer crosslinked with a sulfo-urethane-silanol polymer.

In some embodiments, the coating comprises an poly(meth)acrylate-based polymer, a urethane-based polymer, a siloxane-based polymer or a combination thereof.

As mentioned above, exemplary urethane-based polymers include the polyurethane NEO-REZ available from DSM.

Exemplary siloxanes include those described in U.S. Pat. No. 5,866,222 (Seth et al.) and U.S. Patent Application Ser. No. 61/579,115 filed on Dec. 22, 2011, titled "Adhesive Article Including Primer Layer and Method of Making the Same". U.S. Pat. No. 5,866,222 describes the modification of release coatings to give non-tacky coatings with higher release values to, for example, block copolymer-based pressure sensitive adhesives, through the use of 1 to 30 weight percent of MQ tackifying resin. Higher release values means that the pressure sensitive adhesive has a greater adhesion to the coating than to non-modified release coating. U.S. Patent Application Ser. No. 61/579,115 describes adhesive articles that include a siloxane adhesive and a substrate, with a primer layer interposed between the siloxane adhesive and the substrate. The primer layer includes a siloxane polyoxamide.

A number of (meth)acrylate-based primers are suitable. Besides the primers described above, a particularly suitable primer is the commercially available solventborne material "3M Adhesion Promoter 2262AT" available from 3M Company, St. Paul, Minn.

The adhesive articles described above may be prepared in a variety of ways. The application of the siloxane-based pressure sensitive adhesive to the breathable conformable backing and the surface treatment of the breathable conformable backing can be done in any sequence or even simultaneously. For example, the breathable conformable backing can be surface treated on one surface, either with a physical treatment or a coating, and then the siloxane-based pressure sensitive adhesive can be applied to the opposite surface of the breathable conformable backing. In other embodiments, the siloxane-based pressure sensitive adhesive may be applied to a surface of the breathable conformable backing, and then the surface treatment of the opposite surface of the breathable conformable backing can be carried out. Additional steps and/or layers may also be included in the preparation of the adhesive articles. For example, if one or more coatings are applied as solventborne or waterborne coatings, one or more drying steps may be included. This drying step may involve air drying or accelerated temperature drying using, for example, a forced air oven. Curing steps may be involved, such as e-beam or gamma irradiation curing of the siloxane-based pressure sensitive adhesive.

In some embodiments, it may be desirable to contact a release liner to the siloxane-based pressure sensitive adhesive layer to protect the adhesive layer. Any suitable release liner can be used. In some instances, the siloxane-based pressure sensitive adhesive layer may be formed on a release liner or carrier film and then laminated to the breathable conformable backing. In other instances, the siloxane-based pressure sensitive adhesive may be coated onto the breathable conformable backing.

Also disclosed herein are adhesive constructions comprising the a first adhesive article such as those described above and a second adhesive article, wherein the second article is releasably adhered to the treated surface of the first adhesive article such that the adhesion of the second adhesive article to the treated surface of the first adhesive article is less than the adhesive strength of the first adhesive article to skin. This differential in adhesion permits the second adhesive article to be removed from the first adhesive article without disrupting the adhesion of the first adhesive article to skin. This permits the first adhesive article to function as a platform attached to the skin from which additional adhesive articles can be attached and removed without the second adhesive article contacting the skin.

In addition to the adhesive articles described above, additional adhesive articles can be used as the first adhesive article in adhesive constructions. These additional adhesive articles comprise an adhesive layer that is coated on a breathable conformable backing such as those described above. The adhesive layer in these constructions may be siloxane-based as described above or it may be non-siloxane-based. Examples of non-siloxane-based adhesive layers include virtually any adhesive that can be used to adhere to skin. In some embodiments, the adhesive layer comprises a (meth)acrylate adhesive, such as those described in PCT Publication WO 2011/109672 (Arita et al.). WO 2011/109672 describes adhesives with excellent skin adhesion and low skin irritation that comprise acrylic adhesive particles with an average diameter of 10-100 micrometers.

Typically, the adhesive layer has an adhesion to skin that is less than the adhesion to skin of the second adhesive article. As has been described previously, this provides the advantage that a wide variety of second adhesive articles that could not be conveniently or safely be directly attached to skin can be used because the second adhesive article is attached to the first adhesive article (platform tape) and not directly to skin. Generally the adhesive layer is less than 1,106 micrometers (40 mils) thick. In some embodiments, the adhesive layer is less than 508 micrometers (20 mils), or even less than 254 micrometers (10 mils) thick.

A wide variety of second adhesive articles are suitable, especially second adhesive articles that include a backing layer, and an adhesive layer, where the adhesive layer comprises a non-siloxane-based pressure sensitive adhesive layer. Examples of such adhesive articles include a wide array of medical tapes and drapes.

The backing layer for the second adhesive article may be any material typically used as a tape backing. Examples of suitable tape backing materials include nonwoven materials, paper, metal foils, polymeric films such as: polyester films (e.g., PET polyethylene terephthalate); polyolefin films, such as polypropylene (e.g., biaxially oriented polypropylene (BOPP)), polyethylene, and mixtures thereof; polyurea films; polyurethane films; poly(meth)acrylate films; cellulose triacetate films; films prepared form renewable materials such as PLA (poly lactic acid); and the like. The backing layer may be a breathable conformable backing such as those described above.

A wide variety of pressure sensitive adhesives are suitable for the adhesive layer of the second adhesive article. The pressure sensitive adhesive may be of the type conventionally used with medical tapes, but since the pressure sensitive adhesive is attached to the platform tape (first adhesive article) and not to the skin of the patient, a wider variety of pressure sensitive adhesives can be used. This flexibility in selecting the pressure sensitive adhesive for the second adhesive article is another advantage of the platform tape.

Pressure sensitive adhesives useful in the second adhesive article include those based on natural rubbers, synthetic rubbers, styrene block copolymers, polyvinyl ethers, acrylics, poly-α-olefins, urethanes or ureas.

Useful natural rubber pressure sensitive adhesives generally contain masticated natural rubber, from 25 parts to 300 parts of one or more tackifying resins to 100 parts of natural rubber, and typically from 0.5 to 2.0 parts of one or more antioxidants. Natural rubber may range in grade from a light pale crepe grade to a darker ribbed smoked sheet and includes such examples as CV-60, a controlled viscosity rubber grade and SMR-5, a ribbed smoked sheet rubber grade.

Tackifying resins used with natural rubbers generally include but are not limited to wood rosin and its hydrogenated derivatives; terpene resins of various softening points, and petroleum-based resins, such as, the "ESCOREZ 1300" series of C5 aliphatic olefin-derived resins from Exxon, and "PICCOLYTE S" series, polyterpenes from Hercules, Inc. Antioxidants are used to retard the oxidative attack on natural rubber, which can result in loss of the cohesive strength of the natural rubber adhesive. Useful antioxidants include but are not limited to amines, such as N—N' di-β-naphthyl-1,4-phenylenediamine, available as "AGERITE D"; phenolics, such as 2,5-di-(t-amyl)hydroquinone, available as "SANTOVAR A", available from Monsanto Chemical Co., tetrakis[methylene 3-(3',5'-di-tert-butyl-4'-hydroxyphenyl)propianate]methane, available as "IRGANOX 1010" from Ciba-Geigy Corp., and 2-2'-methylenebis(4-methyl-6-tert butyl phenol), available as Antioxidant 2246; and dithiocarbamates, such as zinc dithiodibutyl carbamate. Other materials can be added to natural rubber adhesives for special purposes, wherein the additions can include plasticizers, pigments, and curing agents to partially vulcanize the pressure sensitive adhesive.

Another useful class of pressure sensitive adhesives are those comprising synthetic rubber. Such adhesives are generally rubbery elastomers, which are either self-tacky or non tacky and require tackifiers.

Self-tacky synthetic rubber pressure sensitive adhesives include for example, butyl rubber, a copolymer of isobutylene with less than 3 percent isoprene, polyisobutylene, a homopolymer of isoprene, polybutadiene, such as "TAKTENE 220 BAYER" or styrene/butadiene rubber. Butyl rubber pressure sensitive adhesives often contain an antioxidant such as zinc dibutyl dithiocarbamate. Polyisobutylene pressure sensitive adhesives do not usually contain antioxidants. Synthetic rubber pressure sensitive adhesives, which generally require tackifiers, are also generally easier to melt process. They comprise polybutadiene or styrene/butadiene rubber, from 10 parts to 200 parts of a tackifier, and generally from 0.5 to 2.0 parts per 100 parts rubber of an antioxidant such as "IRGANOX 1010". An example of a synthetic rubber is "AMERIPOL 1011A", a styrene/butadiene rubber available from BF Goodrich. Tackifiers that are useful include derivatives of rosins such as "FORAL 85", a stabilized rosin ester from Hercules, Inc., the "SNOWTACK" series of gum rosins from Tenneco, and the "AQUATAC" series of tall oil rosins from Sylvachem; and synthetic hydrocarbon resins such as the "PICCOLYTE A" series, polyterpenes from Hercules, Inc., the "ESCOREZ 1300" series of $C_5$ aliphatic olefin-derived resins, the "ESCOREZ 2000" Series of $C_9$ aromatic/aliphatic olefin-derived resins, and polyaromatic $C_9$ resins, such as the "PICCO 5000" series of aromatic hydrocarbon resins, from Hercules, Inc. Other materials can be added for special purposes, including hydrogenated butyl rubber, pigments, plasticizers, liquid rubbers, such as "VISTANEX LMMH" polyisobutylene liquid rubber available from Exxon, and curing agents to vulcanize the adhesive partially.

Styrene block copolymer pressure sensitive adhesives generally comprise elastomers of the A-B or A-B-A type, where A represents a thermoplastic polystyrene block and B represents a rubbery block of polyisoprene, polybutadiene, or poly(ethylene/butylene), and resins. Examples of the various block copolymers useful in block copolymer pressure sensitive adhesives include linear, radial, star and tapered styrene-isoprene block copolymers such as "KRATON D1107P", available from Shell Chemical Co., and "EUROPRENE SOL TE 9110", available from EniChem Elastomers Americas, Inc.; linear styrene-(ethylene-butylene) block copolymers such as "KRATON G1657", available from Shell Chemical Co.; linear styrene-(ethylene-propylene) block copolymers such as "KRATON G1750X", available from Shell Chemical Co.; and linear, radial, and star styrene-butadiene block copolymers such as "KRATON D1118X", available from Shell Chemical Co., and "EUROPRENE SOL TE 6205", available from EniChem Elastomers Americas, Inc. The polystyrene blocks tend to form domains in the shape of spheroids, cylinders, or plates that causes the block copolymer pressure sensitive adhesives to have two phase structures. Resins that associate with the rubber phase generally develop tack in the pressure sensitive adhesive. Examples of rubber phase associating resins include aliphatic olefin-derived resins, such as the "ESCOREZ 1300" series and the "WINGTACK" series, available from Goodyear; rosin esters, such as the "FORAL" series and the "STAYBELITE" Ester 10, both available from Hercules, Inc.; hydrogenated hydrocarbons, such as the "ESCOREZ 5000" series, available from Exxon; polyterpenes, such as the "PICCOLYTE A" series; and terpene phenolic resins derived from petroleum or terpentine sources, such as "PICCOFYN A100", available from Hercules, Inc. Resins that associate with the thermoplastic phase tend to stiffen the pressure sensitive adhesive. Thermoplastic phase associating resins include polyaromatics, such as the "PICCO 6000" series of aromatic hydrocarbon resins, available from Hercules, Inc.; coumarone-indene resins, such as the "CUMAR" series, available from Neville; and other high-solubility parameter resins derived from coal tar or petroleum and having softening points above about 85° C., such as the "AMOCO 18" series of alphamethyl styrene resins, available from Amoco, "PICCOVAR 130" alkyl aromatic polyindene resin, available from Hercules, Inc., and the "PICCOTEX" series of alphamethyl styrene/vinyl toluene resins, available from Hercules. Other materials can be added for special purposes, including rubber phase plasticizing hydrocarbon oils, such as, "TUFFLO 6056", available from Lydondell Petrochemical Co., Polybutene-8 from Chevron, "KAYDOL", available from Witco, and "SHELLFLEX 371", available from Shell Chemical Co.; pigments; antioxidants, such as "IRGANOX 1010" and "IRGANOX 1076", both available from Ciba-Geigy Corp., "BUTAZATE", available from Uniroyal Chemical Co., "CYANOX LDTP", available from American Cyanamid, and "BUTASAN", available from Monsanto Co.; antiozonants, such as "NBC", a nickel dibutyldithiocarbamate, available from DuPont; liquid rubbers such as "VISTANEX LMMH" polyisobutylene rubber; and ultraviolet light inhibitors, such as "IRGANOX 1010" and "TINUVIN P", available from Ciba-Geigy Corp.

Polyvinyl ether pressure sensitive adhesives are generally blends of homopolymers of vinyl methyl ether, vinyl ethyl ether or vinyl iso-butyl ether, or blends of homopolymers of vinyl ethers and copolymers of vinyl ethers and acrylates to achieve desired pressure sensitive properties. Depending on the degree of polymerization, homopolymers may be viscous oils, tacky soft resins or rubber-like substances. Polyvinyl ethers used as raw materials in polyvinyl ether adhesives include polymers based on: vinyl methyl ether such as "LUTANOL M 40", available from BASF, and "GANTREZ M 574" and "GANTREZ 555", available from ISP Technologies, Inc.; vinyl ethyl ether such as "LUTANOL A 25", "LUTANOL A 50" and "LUTANOL A 100"; vinyl isobutyl ether such as "LUTANOL I30", "LUTANOL I60", "LUTANOL IC", "LUTANOL I60D" and "LUTANOL I 65D"; methacrylate/vinyl isobutyl ether/acrylic acid such as "ACRONAL 550 D", available from BASF. Antioxidants useful to stabilize the polyvinylether pressure sensitive adhesive include, for example, "IONOX 30" available from Shell, "IRGANOX 1010" available from Ciba-Geigy, and antioxidant "ZKF" available from Bayer Leverkusen. Other materials can be added for special purposes as described in BASF literature including tackifier, plasticizer and pigments.

Acrylic pressure sensitive adhesives generally have a glass transition temperature of about −20° C. or less and may comprise from 100 to 80 weight percent of a $C_3$-$C_{12}$ alkyl ester component such as, for example, isooctyl acrylate, 2-ethyl-hexyl acrylate and n-butyl acrylate and from 0 to 20 weight percent of a polar component such as, for example, acrylic acid, methacrylic acid, ethylene vinyl acetate, N-vinyl pyrrolidone and styrene macromer. Preferably, the acrylic pressure sensitive adhesives comprise from 0 to 20 weight percent of acrylic acid and from 100 to 80 weight percent of isooctyl acrylate. The acrylic pressure sensitive adhesives may be self-tacky or tackified. Useful tackifiers for acrylics are rosin esters such as "FORAL 85", available from Hercules, Inc., aromatic resins such as "PICCOTEX LC-55WK", aliphatic resins such as "PICCOTAC 95", available from Hercules, Inc., and terpene resins such as α-pinene and β-pinene, available as "PICCOLYTE A-115" and "ZONAREZ B-100" from Arizona Chemical Co. Other materials can be added for special purposes, including hydrogenated butyl rubber, pigments, and curing agents to vulcanize the adhesive partially.

Poly-α-olefin pressure sensitive adhesives, also called a poly(1-alkene) pressure sensitive adhesives, generally comprise either a substantially uncrosslinked polymer or a uncrosslinked polymer that may have radiation activatable functional groups grafted thereon as described in U.S. Pat. No. 5,209,971 (Babu, et al) which is incorporated herein by reference. The poly-α-olefin polymer may be self tacky and/or include one or more tackifying materials. If uncrosslinked, the inherent viscosity of the polymer is generally between about 0.7 and 5.0 dL/g as measured by ASTM D 2857-93, "Standard Practice for Dilute Solution Viscosity of Polymers". In addition, the polymer generally is predominantly amorphous. Useful poly-α-olefin polymers include, for example, $C_3$-$C_{18}$ poly(1-alkene) polymers, preferably $C_5$-$C_{12}$ α-olefins and copolymers of those with $C_3$ and more preferably $C_6$-$C_8$ and copolymers of those with $C_3$. Tackifying materials are typically resins that are miscible in the poly-α-olefin polymer. The total amount of tackifying resin in the poly-α-olefin polymer ranges between 0 to 150 parts by weight per 100 parts of the poly-α-olefin polymer depending on the specific application. Useful tackifying resins include resins derived by polymerization of $C_5$ to $C_9$ unsaturated hydrocarbon monomers, polyterpenes, synthetic polyterpenes and the like. Examples of such commercially available resins based on a $C_5$ olefin fraction of this type are "WINGTACK 95" and "WINGTACK 15" tackifying resins available from Goodyear Tire and Rubber Co. Other hydrocarbon resins include "REGALREZ 1078" and "REGALREZ 1126" available from Hercules Chemical Co., and "ARKON P115" available from Arakawa Chemical Co. Other materials can be added for special purposes, including antioxidants, fillers, pigments, and radiation activated crosslinking agents.

Polyurethane and polyurea pressure sensitive adhesives useful for use in this disclosure include, for example, those disclosed in WO 00/75210 (Kinning et al.) and in U.S. Pat. No. 3,718,712 (Tushaus); U.S. Pat. No. 3,437,622 (Dahl); and U.S. Pat. No. 5,591,820 (Kydonieus et al.).

In many embodiments, the second adhesive article is applied to the first adhesive article to hold a medical article in place. Generally, the first adhesive article is not penetrated by the medical article. Examples or suitable medical articles include cannulas, tubing, catheters, dressings, drapes, or devices for holding medical devices. Cannulas includes a wide range of skin penetrating devices such as needles used to administer intravenous fluids, as well as drains, etc. Devices for holding medical devices includes hooks, loops, tabs or other articles which can be used to hold in place tubing, dressings, drapes or other medical devices or articles. For example, a hook shaped device can be attached to the platform tape by the second adhesive article to hold in place tubing for an IV or a drain. Because the tubing is held by the hook instead of being adhesively bound, the tubing is able to slide more freely.

Another example of a second adhesive article is one which comprises an adhesive layer, a support layer and a layer comprising a reclosable fastener. Examples of reclosable fasteners include hook-and-loop fasteners (commercially available from Velcro, 3M Company, and others) and DUAL LOCK Reclosable Fasteners commercially available from 3M Company. The layer of reclosable fastener can then be used to hold in place a drape or dressing. When the drape or dressing is replaced or checked, it can be detached from the reclosable fastener layer without disrupting the adhesive bond to the patient's skin.

The adhesive articles of this disclosure can be used in a wide variety of ways to prepare adhesive constructions. The adhesive articles are generally used as platform tapes. The platform tape is adhered to the surface of a substrate, typically the skin of a patient. A second adhesive article, as described above, can then be attached to the treated surface of the platform tape. In some embodiments, a medical article or device is contacted to the treated surface of the platform tape prior to the attachment of second adhesive article. Typically the medical article or device is not an adhesive article and the second adhesive article adhesively attaches the medical article to the platform tape. Examples of suitable medical articles and devices include cannulas, tubing, catheters, dressings, drapes, or devices for holding medical devices, as described above.

In some embodiments, the second adhesive article is removed from the treated surface of the platform tape. The second adhesive article may be temporarily removed or permanently removed. For example, the second adhesive article may be temporarily removed to adjust the device that it is holding attached to the platform tape. The second adhesive article may be permanently removed if the device it is holding attached to the platform tape is removed from the patient or changed with a fresh article. Examples of such articles include for example IVs, drains, and dressings. If the second adhesive article is permanently removed, a third adhesive article can be attached to the treated surface of the platform tape to adhere a different or replacement medical device. The third adhesive article may be the same or different from the second adhesive article. The removal and replacement of adhesive articles can be carried out repeatedly as needed or desired.

When desired, either at the completion of treatment or at any other desired time, the platform tape can be removed from the skin surface of the patient.

The present disclosure includes the following embodiments.

Among the embodiments are adhesive articles. The first embodiment includes an adhesive article comprising: a siloxane-based pressure sensitive adhesive layer; and a breathable conformable backing comprising a first surface and a second surface, wherein the siloxane-based pressure sensitive adhesive layer is coated on the first surface of the breathable conformable backing, and wherein the second surface of the breathable conformable backing comprises a treated surface, wherein the treated surface is not a pressure sensitive adhesive and wherein the treated surface provides increased adhesion to non-siloxane-based pressure sensitive adhesives when compared to the adhesion to the same backing without the treated surface.

Embodiment 2 is the adhesive article of embodiment 1, wherein the siloxane-based pressure sensitive adhesive comprises an elastomeric siloxane polymer prepared from an amine-functional polysiloxane, a hydroxyl-functional polysiloxane, a hydride-functional polysiloxane, an alkoxysilane-functional polysiloxane, a vinyl-functional polysiloxane, an allyl-functional polysiloxane, a (meth)acrylate-functional polysiloxane, a non-functional polysiloxanes or a combination thereof.

Embodiment 3 is the adhesive article of embodiment 2, wherein elastomeric siloxane polymer comprises a urea-based siloxane copolymer, oxamide-based siloxane copolymer, amide-based siloxane copolymer, urethane-based siloxane copolymer, and mixtures thereof.

Embodiment 4 is the adhesive article of embodiment 2, wherein the elastomeric siloxane polymer comprises a polysiloxane polymer or copolymer prepared by the electron beam crosslinking of at least one nonfunctionalized siloxane material.

Embodiment 5 is the adhesive article of embodiment 4, wherein the at least one nonfunctionalized siloxane material comprises a nonfunctionalized poly(dialkylsiloxane).

Embodiment 6 is the adhesive article of embodiment 5, wherein the nonfunctionalized poly(dialkylsiloxane) material comprises alkyl and/or hydroxyl groups.

Embodiment 7 is the adhesive article of any of embodiments 4-6, wherein the nonfunctionalized siloxane material comprises a siloxane oil or fluid.

Embodiment 8 is the adhesive article of any of embodiments 1-7, wherein the siloxane-based pressure sensitive adhesive further comprises at least one tackifying resin.

Embodiment 9 is the adhesive article of embodiment 8, wherein the tackifying resin comprises one or more MQ resins.

Embodiment 10 is the adhesive article of any of embodiments 1-9, wherein the treated surface of the breathable conformable backing is prepared by physical treatment, a coating, or a combination thereof.

Embodiment 11 is the adhesive article of embodiment 10, wherein the physical treatment comprises flame treatment, corona treatment, plasma treatment, or a combination thereof.

Embodiment 12 is the adhesive article of embodiment 10, wherein the coating comprises a polyamide, a poly(meth)acrylate, a polyolefin, a natural rubber, a synthetic rubber, a polyurethane, a polyurea, a siloxane, a silane, a polyester, an epoxy, a polycarbodiimide, a phenolic, or a combination thereof.

Embodiment 13 is the adhesive article of embodiment 10, wherein the coating comprises a poly(meth)acrylate-based polymer, a urethane-based polymer, a siloxane-containing polymer or a combination thereof.

Embodiment 14 is the adhesive article of any of embodiments 1-13, wherein the breathable conformable backing comprises a paper backing, a woven or knit textile backing, a nonwoven backing, or a breathable plastic backing.

Embodiment 15 is the adhesive article of any of embodiments 1-14, wherein the breathable conformable backing comprises a porous backing.

Among the embodiments are adhesive constructions. Embodiment 16 is an adhesive construction comprising: a first adhesive article comprising: a siloxane-based pressure sensitive adhesive layer; and a breathable conformable backing comprising a first surface and a second surface, wherein the siloxane-based pressure sensitive adhesive layer is coated on the first surface of the breathable conformable backing, and wherein the second surface of the breathable conformable backing comprises a treated surface, wherein the treated surface is not a pressure sensitive adhesive and wherein the treated surface provides increased adhesion to non-siloxane-based pressure sensitive adhesives when compared to the adhesion of the same backing without the treated surface; and a second adhesive article, wherein the second article is adhered to the treated surface of the first adhesive article.

Embodiment 17 is the adhesive construction of embodiment 16, wherein the second adhesive article is releasably adhered to the treated surface of the first adhesive article such that the adhesion of the second adhesive article for the treated surface of the first adhesive article is less than the adhesion of the first adhesive article to skin.

Embodiment 18 is the adhesive construction of embodiment 16 or 17, wherein the siloxane-based pressure sensitive adhesive comprises an elastomeric siloxane polymer prepared from an amine-functional polysiloxane, a hydroxyl-functional polysiloxane, a hydride-functional polysiloxane, an alkoxysilane-functional polysiloxane, a vinyl-functional polysiloxane, an allyl-functional polysiloxane, a (meth)acrylate-functional polysiloxane, a non-functional polysiloxanes or a combination thereof.

Embodiment 19 is the adhesive construction of embodiment 18, wherein the elastomeric siloxane polymer comprises a polysiloxane polymer or copolymer prepared by the electron beam crosslinking of at least one nonfunctionalized siloxane material.

Embodiment 20 is the adhesive construction of embodiment 19, wherein the at least one nonfunctionalized siloxane material comprises a nonfunctionalized poly(dialkylsiloxane).

Embodiment 21 is the adhesive construction of embodiment 20, wherein the nonfunctionalized poly(dialkylsiloxane) material comprises alkyl and/or hydroxyl groups.

Embodiment 22 is the adhesive construction of any of embodiments 19-21, wherein the nonfunctionalized siloxane material comprises a siloxane oil or fluid.

Embodiment 23 is the adhesive construction of any of embodiments 16-22, wherein the siloxane-based pressure sensitive adhesive further comprises at least one tackifying resin.

Embodiment 24 is the adhesive construction of embodiment 23, wherein the tackifying resin comprises one or more MQ resins.

Embodiment 25 is the adhesive construction of any of embodiments 16-24, wherein the treated surface of the breathable conformable backing is prepared by physical treatment, a coating, or a combination thereof.

Embodiment 26 is the adhesive construction of embodiment 25, wherein the physical treatment comprises flame treatment, corona treatment, plasma treatment, or a combination thereof.

Embodiment 27 is the adhesive construction of embodiment 25, wherein the coating comprises a polyamide, a poly(meth)acrylate, a polyolefin, a natural rubber, a synthetic rubber, a polyurethane, a polyurea, a siloxane, a silane, a polyester, an epoxy, a polycarbodiimide, a phenolic, or a combination thereof.

Embodiment 28 is the adhesive construction of embodiment 25, wherein the coating comprises a poly(meth)acrylate-based polymer, a urethane-based polymer, a siloxane-containing polymer or a combination thereof.

Embodiment 29 is the adhesive construction of any of embodiments 16-28, wherein the breathable conformable backing comprises a paper backing, a woven or knit textile backing, a nonwoven backing, or a breathable plastic backing.

Embodiment 30 is the adhesive construction of any of embodiments 16-29, wherein the breathable conformable backing comprises a porous backing.

Embodiment 31 is the adhesive construction of any of embodiments 16-30, wherein the second adhesive article comprises: a backing layer; and an adhesive layer, wherein the adhesive layer comprises a nonsiloxane-based pressure sensitive adhesive layer.

Embodiment 32 is the adhesive construction of any of embodiments 16-31, further comprising a medical article located between the first adhesive article and the second adhesive article.

Embodiment 33 is the adhesive construction of embodiment 32, wherein the medical article located between the first adhesive article and the second adhesive article comprises a cannula, tubing, a catheter, a dressing, a drape or a device for holding a medical device.

Embodiment 34 is the adhesive construction of any of embodiments 16-30, wherein the second adhesive article comprises an adhesive layer and layer comprising a reclosable fastener.

Embodiment 35 is an adhesive construction comprising: a first adhesive article comprising: an adhesive layer; and a breathable conformable backing comprising a first surface and a second surface, wherein the adhesive layer is coated on the first surface of the breathable conformable backing, and wherein the second surface of the breathable conformable backing comprises a treated surface, wherein the treated surface is not a pressure sensitive adhesive and wherein the treated surface provides increased adhesion to non-siloxane-based pressure sensitive adhesives when compared to the adhesion of the same backing without the treated surface; and a second adhesive article, wherein the second adhesive article is adhered to the treated surface of the first adhesive article, and wherein the adhesion to skin of the first adhesive article is greater than the adhesion to skin of the second adhesive article.

Embodiment 36 is the adhesive construction of embodiment 35, wherein the adhesive layer of the first adhesive article has a thickness of less than 1,016 micrometers (40 mils).

Embodiment 37 is the adhesive construction of embodiment 35, wherein the adhesive layer of the first adhesive article has a thickness of less than 508 micrometers (20 mils).

Embodiment 38 is the adhesive construction of embodiment 35, wherein the adhesive layer of the first adhesive article has a thickness of less than 254 micrometers (10 mils).

Embodiment 39 is the adhesive construction of any of embodiments 35-38, wherein the second adhesive article is releasably adhered to the treated surface of the first adhesive article such that the adhesion of the second adhesive article for the treated surface of the first adhesive article is less than the adhesion of the first adhesive article to skin.

Embodiment 40 is the adhesive construction of any of embodiments 35-39, wherein the adhesive layer comprises a pressure sensitive adhesive.

Embodiment 41 is the adhesive construction of embodiment 40, wherein the pressure sensitive adhesive comprises a siloxane-based pressure sensitive adhesive or a (meth)acrylate-based pressure sensitive adhesive.

Embodiment 42 is the adhesive construction of embodiment 41, wherein the (meth)acrylate-based pressure sensitive adhesive comprises a composition with acrylic adhesive particles having an average diameter of 10-100 micrometers.

Embodiment 43 is the adhesive construction of embodiment 41, wherein the siloxane-based pressure sensitive adhesive comprises an elastomeric siloxane polymer prepared from an amine-functional polysiloxane, a hydroxyl-functional polysiloxane, a hydride-functional polysiloxane, an alkoxysilane-functional polysiloxane, a vinyl-functional polysiloxane, an allyl-functional polysiloxane, a (meth)acrylate-functional polysiloxane, a non-functional polysiloxanes or a combination thereof.

Embodiment 44 is the adhesive construction of embodiment 43, wherein the elastomeric siloxane polymer comprises a polysiloxane polymer or copolymer prepared by the electron beam crosslinking of at least one nonfunctionalized siloxane material.

Embodiment 45 is the adhesive construction of embodiment 44, wherein the at least one nonfunctionalized siloxane material comprises a nonfunctionalized poly(dialkylsiloxane).

Embodiment 46 is the adhesive construction of embodiment 45, wherein the nonfunctionalized poly(dialkylsiloxane) material comprises alkyl and/or hydroxyl groups.

Embodiment 47 is the adhesive construction of any of embodiments 44-46, wherein the nonfunctionalized siloxane material comprises a siloxane oil or fluid.

Embodiment 48 is the adhesive construction of any of embodiments 44-47, wherein the siloxane-based pressure sensitive adhesive further comprises at least one tackifying resin.

Embodiment 49 is the adhesive construction of embodiment 48, wherein the tackifying resin comprises one or more MQ resins.

Embodiment 50 is the adhesive construction of any of embodiments 35-49, wherein the treated surface of the breathable conformable backing is prepared by physical treatment, a coating, or a combination thereof.

Embodiment 51 is the adhesive construction of embodiment 50, wherein the physical treatment comprises flame treatment, corona treatment, plasma treatment, or a combination thereof.

Embodiment 52 is the adhesive construction of embodiment 50, wherein the coating comprises a polyamide, a poly(meth)acrylate, a polyolefin, a natural rubber, a synthetic rubber, a polyurethane, a polyurea, a siloxane, a silane, a polyester, an epoxy, a polycarbodiimide, a phenolic, or a combination thereof.

Embodiment 53 is the adhesive construction of embodiment 50, wherein the coating comprises a poly(meth)acrylate-based polymer, a urethane-based polymer, a siloxane-containing polymer or a combination thereof.

Embodiment 54 is the adhesive construction of any of embodiments 35-53, wherein the breathable conformable backing comprises a paper backing, a woven or knit textile backing, a nonwoven backing, or a breathable plastic backing.

Embodiment 55 is the adhesive construction of any of embodiments 35-54, wherein the breathable conformable backing comprises a porous backing.

Embodiment 56 is the adhesive construction of any of embodiments 35-55, wherein the second adhesive article comprises: a backing layer; and an adhesive layer, wherein the adhesive layer comprises a nonsiloxane-based pressure sensitive adhesive layer.

Embodiment 57 is the adhesive construction of any of embodiments 35-56, further comprising a medical article located between the first adhesive article and the second adhesive article.

Embodiment 58 is the adhesive construction of embodiment 57, wherein the medical article located between the first adhesive article and the second adhesive article comprises a cannula, tubing, a catheter, a dressing, a drape or a device for holding a medical device.

Embodiment 59 is the adhesive construction of any of embodiments 35-55, wherein the second adhesive article comprises an adhesive layer and layer comprising a reclosable fastener.

Among the embodiments are methods of preparing adhesive constructions. Embodiment 60 is a method of preparing an adhesive construction comprising: providing a first adhesive article, wherein the first adhesive article comprises: a siloxane-based pressure sensitive adhesive layer; and a breathable conformable backing comprising a first surface and a second surface, wherein the siloxane-based pressure sensitive adhesive layer is coated on the first surface of the breathable conformable backing, and wherein the second surface of the breathable conformable backing comprises a treated surface, wherein the treated surface is not a pressure sensitive adhesive and wherein the treated surface provides increased adhesion to non-siloxane pressure sensitive adhesives when compared to the same backing without the treated surface; applying the first adhesive article to a skin surface; providing a second adhesive article; and applying the second adhesive article to the treated surface of the first adhesive article.

Embodiment 61 is the method of embodiment 60, further comprising applying a medical article to at least a portion of the treated surface of the first adhesive article prior to application of the second adhesive article to the treated surface of the first adhesive article.

Embodiment 62 is the method of embodiment 61, wherein the medical article comprises tubing, a catheter, a dressing, a drape, or a device for holding a medical device.

Embodiment 63 is the method of any of claims 60-62, further comprising: removing the second adhesive article from the treated surface of the first adhesive article; providing a third adhesive article; and applying the third adhesive article to the treated surface of the first adhesive article.

Embodiment 64 is the method of any of embodiments 60-63, wherein the second adhesive article is releasably adhered to the treated surface of the first adhesive article such that the adhesion of the second adhesive article for the treated surface of the first adhesive article is less than the adhesion of the first adhesive article to skin.

Embodiment 65 is the method of any of embodiments 60-64, wherein the siloxane-based pressure sensitive adhesive comprises an elastomeric siloxane polymer prepared from an amine-functional polysiloxane, a hydroxyl-functional polysiloxane, a hydride-functional polysiloxane, an alkoxysilane-functional polysiloxane, a vinyl-functional polysiloxane, an allyl-functional polysiloxane, a (meth)acrylate-functional polysiloxane, a non-functional polysiloxane or a combination thereof.

Embodiment 66 is the method of embodiment 65, wherein the elastomeric siloxane polymer comprises a polysiloxane polymer or copolymer prepared by the electron beam crosslinking of at least one nonfunctionalized siloxane material.

Embodiment 67 is the method of embodiment 66, wherein the at least one nonfunctionalized siloxane material comprises a nonfunctionalized poly(dialkylsiloxane).

Embodiment 68 is the method of embodiment 67, wherein the nonfunctionalized poly(dialkylsiloxane) material comprises alkyl and/or hydroxyl groups.

Embodiment 69 is the method of any of embodiments 65-68, wherein the nonfunctionalized siloxane material comprises a siloxane oil or fluid.

Embodiment 70 is the method of any of embodiments 60-69, wherein the siloxane-based pressure sensitive adhesive further comprises at least one tackifying resin.

Embodiment 71 is the method of embodiment 70, wherein the tackifying resin comprises one or more MQ resins.

Embodiment 72 is the method of any of embodiments 60-71, wherein the treated surface of the breathable conformable backing is prepared by physical treatment, a coating, or a combination thereof.

Embodiment 73 is the method of embodiment 72, wherein the physical treatment comprises flame treatment, corona treatment, plasma treatment, or a combination thereof.

Embodiment 74 is the method of embodiment 72, wherein the coating comprises a polyamide, a poly(meth)acrylate, a polyolefin, a natural rubber, a synthetic rubber, a polyurethane, a polyurea, a siloxane, a silane, a polyester, an epoxy, a polycarbodiimide, a phenolic, or a combination thereof.

Embodiment 75 is the method of embodiment 72, wherein the coating comprises a poly(meth)acrylate-based polymer, a urethane-based polymer, a siloxane-containing polymer or a combination thereof.

Embodiment 76 is the method of any of embodiments 60-75, wherein the breathable conformable backing comprises a paper backing, a woven or knit textile backing, a nonwoven backing, or a breathable plastic backing.

Embodiment 77 is the method of any of embodiments 60-76, wherein the breathable conformable backing comprises a porous backing.

Embodiment 78 is the method of any of embodiments 60-77, wherein the second adhesive article comprises: a backing layer; and an adhesive layer, wherein the adhesive layer comprises a nonsiloxane-based pressure sensitive adhesive layer.

Embodiment 79 is the method of any of embodiments 60-78, further comprising a medical article located between the first adhesive article and the second adhesive article.

Embodiment 80 is the method of embodiment 79, wherein the medical article located between the first adhesive article and the second adhesive article comprises a cannula, tubing, a catheter, a dressing, a drape or a device for holding a medical device.

Embodiment 81 is the method of any of embodiments 60-77, wherein the second adhesive article comprises an adhesive layer and layer comprising a reclosable fastener.

Embodiment 82 is a method of preparing an adhesive construction comprising: providing a first adhesive article, wherein the first adhesive article comprises: an adhesive layer; and a breathable conformable backing comprising a first surface and a second surface, wherein the adhesive layer is coated on the first surface of the breathable conformable backing, and wherein the second surface of the breathable conformable backing comprises a treated surface, wherein the treated surface is not a pressure sensitive adhesive and wherein the treated surface provides increased adhesion to non-siloxane pressure sensitive adhesives when compared to the same backing without the treated surface; applying the first adhesive article to a skin surface; providing a second adhesive article, wherein the second adhesive article has an adhesion to skin that is greater than the adhesion to skin of the first adhesive article; and applying the second adhesive article to the treated surface of the first adhesive article.

Embodiment 83 is the method of embodiment 82, further comprising applying a medical article to at least a portion of the treated surface of the first adhesive article prior to application of the second adhesive article to the treated surface of the first adhesive article.

Embodiment 84 is the method of embodiment 83, wherein the medical article comprises tubing, a catheter, a dressing, a drape, or a device for holding a medical device.

Embodiment 85 is the method of any of claims 82-84, further comprising: removing the second adhesive article from the treated surface of the first adhesive article; providing a third adhesive article; and applying the third adhesive article to the treated surface of the first adhesive article.

Embodiment 86 is the method of any of embodiments 82-85, wherein the second adhesive article is releasably adhered to the treated surface of the first adhesive article such that the adhesion of the second adhesive article for the treated surface of the first adhesive article is less than the adhesion of the first adhesive article to skin.

Embodiment 87 is the method of any of embodiments 82-86, wherein the adhesive layer of the first adhesive article has a thickness of less than 1,016 micrometers (40 mils).

Embodiment 88 is the method of any of embodiments 82-86, wherein the adhesive layer of the first adhesive article has a thickness of less than 508 micrometers (20 mils).

Embodiment 89 is the method of any of embodiments 82-86, wherein the adhesive layer of the first adhesive article has a thickness of less than 254 micrometers (10 mils).

Embodiment 90 is the method of any of embodiments 82-89, wherein the adhesive layer comprises a pressure sensitive adhesive.

Embodiment 91 is the method of embodiment 90, wherein the pressure sensitive adhesive comprises a siloxane-based pressure sensitive adhesive or a (meth)acrylate-based pressure sensitive adhesive.

Embodiment 92 is the method of embodiment 91, wherein the (meth)acrylate-based pressure sensitive adhesive comprises a composition with acrylic adhesive particles having an average diameter of 10-100 micrometers.

Embodiment 93 is the method of embodiment 91, wherein the siloxane-based pressure sensitive adhesive comprises an elastomeric siloxane polymer prepared from an amine-functional polysiloxane, a hydroxyl-functional polysiloxane, a hydride-functional polysiloxane, an alkoxysilane-functional polysiloxane, a vinyl-functional polysiloxane, an allyl-functional polysiloxane, a (meth)acrylate-functional polysiloxane, a non-functional polysiloxanes or a combination thereof.

Embodiment 94 is the method of embodiment 93, wherein the elastomeric siloxane polymer comprises a polysiloxane polymer or copolymer prepared by the electron beam cross-linking of at least one nonfunctionalized siloxane material.

Embodiment 95 is the method of embodiment 94, wherein the at least one nonfunctionalized siloxane material comprises a nonfunctionalized poly(dialkylsiloxane).

Embodiment 96 is the method of embodiment 95, wherein the nonfunctionalized poly(dialkylsiloxane) material comprises alkyl and/or hydroxyl groups.

Embodiment 97 is the method of any of embodiments 94-96, wherein the nonfunctionalized siloxane material comprises a siloxane oil or fluid.

Embodiment 98 is the method of any of embodiments 94-97, wherein the siloxane-based pressure sensitive adhesive further comprises at least one tackifying resin.

Embodiment 99 is the method of embodiment 98, wherein the tackifying resin comprises one or more MQ resins.

Embodiment 100 is the method of any of embodiments 82-99, wherein the treated surface of the breathable conformable backing is prepared by physical treatment, a coating, or a combination thereof.

Embodiment 101 is the method of embodiment 100, wherein the physical treatment comprises flame treatment, corona treatment, plasma treatment, or a combination thereof.

Embodiment 102 is the method of embodiment 100, wherein the coating comprises a polyamide, a poly(meth)acrylate, a polyolefin, a natural rubber, a synthetic rubber, a polyurethane, a polyurea, a siloxane, a silane, a polyester, an epoxy, a polycarbodiimide, a phenolic, or a combination thereof.

Embodiment 103 is the method of embodiment 100, wherein the coating comprises a poly(meth)acrylate-based polymer, a urethane-based polymer, a siloxane-containing polymer or a combination thereof.

Embodiment 104 is the method of any of embodiments 82-103, wherein the breathable conformable backing comprises a paper backing, a woven or knit textile backing, a nonwoven backing, or a breathable plastic backing.

Embodiment 105 is the method of any of embodiments 82-104, wherein the breathable conformable backing comprises a porous backing.

Embodiment 106 is the method of any of embodiments 82-105, wherein the second adhesive article comprises: a backing layer; and an adhesive layer, wherein the adhesive layer comprises a nonsiloxane-based pressure sensitive adhesive layer.

Embodiment 107 is the method of any of embodiments 82-106, further comprising a medical article located between the first adhesive article and the second adhesive article.

Embodiment 108 is the method of embodiment 107, wherein the medical article located between the first adhesive article and the second adhesive article comprises a cannula, tubing, a catheter, a dressing, a drape or a device for holding a medical device.

Embodiment 109 is the method of any of embodiments 82-105, wherein the second adhesive article comprises an adhesive layer and layer comprising a reclosable fastener.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted. The following abbreviations are used: g=grams; cm=centimeters; kg=kilograms; min=minutes; mL=milliliters. The terms "weight %", "% by weight", and "wt %" are used interchangeably.

| Table of Abbreviations | |
|---|---|
| Material | Description |
| Sample Tape | Medical tape commercially available from 3M Company, St. Paul, MN as "KIND REMOVAL TAPE". |
| Tape-1 | Medical tape commercially available from 3M Company, St. Paul, MN as "MICROPORE". |
| Tape-2 | Medical tape commercially available from 3M Company, St. Paul, MN as "TRANSPORE". |
| Tape-3 | Medical tape commercially available from 3M Company, St. Paul, MN as "DURAPORE". |
| Tape-4 | Medical tape commercially available from 3M Company, St. Paul, MN as "TRANSPORE WHITE". |
| Tape-5 | Medical tape commercially available from 3M Company, St. Paul, MN as "MEDIPORE H". |
| Tape-6 | Medical tape commercially available from 3M Company, St. Paul, MN as "MICROPORE PLUS". |
| Coating Solution | A 10% solids solventborne material commercially available from 3M Company, St. Paul, MN as "3M Adhesion Promoter 2262AT". |

Test Methods
Adhesion Test

The platform tape to be tested was placed on a 5 cm by 13 cm AISI#302 or 304 stainless steel panel, and adhered with two passes of a 2 kg roller. A piece of a commercially available test tape was placed on the platform tape and adhered with two passes of a 2 kg roller. A Zwick/Roell Z005 force transducer (Zwick USA, Kennesaw, Ga.) was then used to peel the commercially available tape from the platform tape at 30 cm/min and a 180° angle. The average peel force was recorded in grams/centimeter (g/cm).

Examples 1-6 and Comparative Examples C1-C6

A siloxane-based adhesive platform tape was prepared by washing the backside coating from samples of Sample Tape with 50 mL of ethyl acetate followed by 50 mL of isopropanol. For Comparative Examples C1-C6, this platform tape was used. For Examples 1-6, Coating Solution was coated with a #5 Mayer rod on the backside of the washed Sample Tape and allowed to dry overnight. The adhesion of several commercially available tapes was tested according to the Adhesion Test Method described above to the coated or uncoated siloxane-based adhesive platform tape. Results are shown in Table 1.

TABLE 1

| Example | Test Tape Identity | Adhesion (g/cm) |
|---|---|---|
| C1 | Tape-1 | 11.4 |
| 1 | Tape-1 | 45.4 |
| C2 | Tape-2 | 13.3 |
| 2 | Tape-2 | 73.8 |
| C3 | Tape-3 | 16.9 |
| 3 | Tape-3 | 103.4 |
| C4 | Tape-4 | 26.2 |
| 4 | Tape-4 | 57.9 |
| C5 | Tape-5 | 23.2 |
| 5 | Tape-5 | 62.8 |
| C6 | Tape-6 | 14.8 |
| 6 | Tape-6 | 41.9 |

What is claimed is:

1. An adhesive article comprising:
a siloxane-based pressure sensitive adhesive layer; and
a breathable conformable backing comprising a first surface and a second surface, wherein the siloxane-based pressure sensitive adhesive layer is disposed on the first surface of the breathable conformable backing, and wherein the second surface of the breathable conformable backing comprises a treated surface, wherein the treated surface is not a pressure sensitive adhesive and wherein the treated surface provides increased adhesion to non-siloxane-based pressure sensitive adhesives when compared to the adhesion to the same backing without the treated surface, and wherein the treated surface of the breathable conformable backing is prepared by a coating, and wherein when the surface treatment includes a single coating, the coating covers the entire second surface of the backing and is a low adhesion backsize (LAB) such that in a roll of the adhesive article where the adhesive layer contacts the treated second surface of the backing, the adhesion of the siloxane-based pressure sensitive adhesive to the treated second surface is sufficiently low that the roll may be unwound.

2. The adhesive article of claim 1, wherein the siloxane-based pressure sensitive adhesive comprises an elastomeric siloxane polymer prepared from an amine-functional polysiloxane, a hydroxyl-functional polysiloxane, a hydride-functional polysiloxane, an alkoxysilane-functional polysiloxane, a vinyl-functional polysiloxane, an allyl-functional polysiloxane, a (meth)acrylate-functional polysiloxane, a non-functional polysiloxanes or a combination thereof.

3. The adhesive article of claim 2, wherein elastomeric siloxane polymer comprises a urea-based siloxane copolymer, oxamide-based siloxane copolymer, amide-based siloxane copolymer, urethane-based siloxane copolymer, and mixtures thereof.

4. The adhesive article of claim 2, wherein the elastomeric siloxane polymer comprises a polysiloxane polymer or copolymer prepared by the electron beam crosslinking of at least one nonfunctionalized siloxane material.

5. The adhesive article of claim 2, wherein the siloxane-based pressure sensitive adhesive further comprises at least one tackifying resin.

6. The adhesive article of claim 1, wherein the coating comprises a polyamide, a poly(meth)acrylate, a polyolefin, a natural rubber, a synthetic rubber, a polyurethane, a polyurea, a siloxane, a silane, a polyester, an epoxy, a polycarbodiimide, a phenolic, or a combination thereof.

7. The adhesive article of claim 6, wherein the coating comprises a poly(meth)acrylate-based polymer, a urethane-based polymer, a siloxane-containing polymer or a combination thereof.

8. The adhesive article of claim 1, wherein the breathable conformable backing comprises a paper backing, a woven or knit textile backing, a nonwoven backing, or a breathable plastic backing.

9. An adhesive construction comprising:
a first adhesive article comprising:
  a siloxane-based pressure sensitive adhesive layer; and
  a breathable conformable backing comprising a first surface and a second surface, wherein the siloxane-based pressure sensitive adhesive layer is coated on the first surface of the breathable conformable backing, and wherein the second surface of the breathable conformable backing comprises a treated surface, wherein the treated surface is not a pressure sensitive adhesive and wherein the treated surface provides increased adhesion to non-siloxane-based pressure sensitive adhesives when compared to the adhesion of the same backing without the treated surface, and wherein the treated surface of the breathable conformable backing is prepared by a coating, and wherein when the surface treatment includes a single coating, the coating covers the entire second surface of the backing and is a low adhesion backsize (LAB) such that in a roll of the adhesive article where the adhesive layer contacts the treated second surface of the backing, the adhesion of the siloxane-based pressure sensitive adhesive to the treated second surface is sufficiently low that the roll may be unwound; and
a second adhesive article, wherein the second article is adhered to the treated surface of the first adhesive article.

10. The adhesive construction of claim 9, wherein the second adhesive article is releasably adhered to the treated surface of the first adhesive article such that the adhesion of the second adhesive article for the treated surface of the first adhesive article is less than the adhesion of the first adhesive article to skin.

11. The adhesive construction of claim 9, wherein the siloxane-based pressure sensitive adhesive comprises an elastomeric siloxane polymer prepared from an amine-functional polysiloxane, a hydroxyl-functional polysiloxane, a hydride-functional polysiloxane, an alkoxysilane-functional polysiloxane, a vinyl-functional polysiloxane, an allyl-functional polysiloxane, a (meth)acrylate-functional polysiloxane, a non-functional polysiloxanes or a combination thereof.

12. The adhesive construction of claim 11, wherein the elastomeric siloxane polymer comprises a polysiloxane polymer or copolymer prepared by the electron beam cross-linking of at least one nonfunctionalized siloxane material.

13. The adhesive construction of claim 9, wherein the treated surface of the breathable conformable backing comprises a coating comprising a polyamide, a poly(meth)acrylate, a polyolefin, a natural rubber, a synthetic rubber, a polyurethane, a polyurea, a siloxane, a silane, a polyester, an epoxy, a polycarbodiimide, a phenolic, or a combination thereof.

14. The adhesive construction of claim 9, wherein the second adhesive article comprises:
a backing layer; and
an adhesive layer, wherein the adhesive layer comprises a nonsiloxane-based pressure sensitive adhesive layer.

15. The adhesive construction of claim 9, further comprising a medical article located between the first adhesive article and the second adhesive article.

16. The adhesive construction of claim 15, wherein the medical article located between the first adhesive article and the second adhesive article comprises a cannula, tubing, a catheter, a dressing, a drape or a device for holding a medical device.

17. A method of preparing an adhesive construction comprising:
providing a first adhesive article, wherein the first adhesive article comprises:
  a siloxane-based pressure sensitive adhesive layer; and
  a breathable conformable backing comprising a first surface and a second surface, wherein the siloxane-based pressure sensitive adhesive layer is coated on the first surface of the breathable conformable backing, and wherein the second surface of the breathable conformable backing comprises a treated surface, wherein the treated surface is not a pressure sensitive adhesive and wherein the treated surface provides increased adhesion to non-siloxane pressure sensitive adhesives when compared to the same backing without the treated surface, and wherein the treated surface of the breathable conformable backing is prepared by a coating, and wherein when the surface treatment includes a single coating, the coating covers the entire second surface of the backing and is a low adhesion backsize (LAB) such that in a roll of the adhesive article where the adhesive layer contacts the treated second surface of the backing, the adhesion of the siloxane-based pressure sensitive adhesive to the treated second surface is sufficiently low that the roll may be unwound;
applying the first adhesive article to a skin surface;
providing a second adhesive article; and
applying the second adhesive article to the treated surface of the first adhesive article.

18. The method of claim 17, further comprising applying a medical article to at least a portion of the treated surface of the first adhesive article prior to application of the second adhesive article to the treated surface of the first adhesive article.

19. The method of claim 18, wherein the medical article comprises tubing, a catheter, a dressing, a drape, or a device for holding a medical device.

20. The method of claim 17, further comprising:
removing the second adhesive article from the treated surface of the first adhesive article;
providing a third adhesive article; and
applying the third adhesive article to the treated surface of the first adhesive article.

* * * * *